(12) United States Patent
Lake et al.

(10) Patent No.: US 10,279,535 B2
(45) Date of Patent: May 7, 2019

(54) METHOD AND APPARATUS FOR DEFORMING A WEB

(71) Applicant: The Procter & Gamble Company, Cincinnati, OH (US)

(72) Inventors: Kirk Wallace Lake, Cincinnati, OH (US); Jill Marlene Orr, Liberty Township, OH (US); John Joseph Curro, Cincinnati, OH (US); John Brian Strube, Okeana, OH (US); Timothy Ian Mullane, Union, KY (US); Leroy Joseph Kocher, Sunman, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 188 days.

(21) Appl. No.: 14/806,681

(22) Filed: Jul. 23, 2015

(65) Prior Publication Data
US 2015/0321414 A1    Nov. 12, 2015

Related U.S. Application Data

(62) Division of application No. 14/147,615, filed on Jan. 6, 2014, now Pat. No. 9,120,268, which is a division
(Continued)

(51) Int. Cl.
*A61F 13/15*    (2006.01)
*B29C 53/24*    (2006.01)
(Continued)

(52) U.S. Cl.
CPC ........ *B29C 53/24* (2013.01); *A61F 13/15707* (2013.01); *B29C 55/18* (2013.01);
(Continued)

(58) Field of Classification Search
CPC ...... Y10T 428/24694; A61F 13/15707; D21H 27/02; D21H 27/40
See application file for complete search history.

(56) References Cited

U.S. PATENT DOCUMENTS

| | | | |
|---|---|---|---|
| 2,068,456 A | 1/1937 | Hooper | |
| 2,275,425 A | 3/1942 | Grabec | |

(Continued)

FOREIGN PATENT DOCUMENTS

| | | |
|---|---|---|
| CN | 102673030 | 9/2012 |
| CN | 202491475 | 10/2012 |

(Continued)

OTHER PUBLICATIONS

U.S. Appl. No. 13/546,015, filed Jul. 11, 2012, Hugh Joseph O'Donnell et al.
(Continued)

*Primary Examiner* — Donald J Loney
(74) *Attorney, Agent, or Firm* — Christian M. Best

(57) ABSTRACT

Methods and apparatuses for deforming a web are disclosed. In one embodiment, the method involves feeding a web into a nip that is formed between at least two intermeshing rolls. The rolls are configured for deforming a web with at least two sets of deformations that are oriented in different directions relative to the surfaces of the web.

19 Claims, 20 Drawing Sheets

Related U.S. Application Data of application No. 13/094,195, filed on Apr. 26, 2011, now Pat. No. 8,657,596.

(51) Int. Cl.

| | | |
|---|---|---|
| *B31F 1/20* | (2006.01) | |
| *B29C 55/18* | (2006.01) | |
| *B31F 1/07* | (2006.01) | |
| *B29C 43/46* | (2006.01) | |
| *B29C 59/04* | (2006.01) | |
| *B29L 7/00* | (2006.01) | |
| *D21H 27/02* | (2006.01) | |
| *D21H 27/40* | (2006.01) | |

(52) U.S. Cl.
CPC .................. *B31F 1/07* (2013.01); *B31F 1/20* (2013.01); *B29C 59/04* (2013.01); *B29C 2043/464* (2013.01); *B29L 2007/002* (2013.01); *B31F 2201/0733* (2013.01); *B31F 2201/0738* (2013.01); *B31F 2201/0741* (2013.01); *B31F 2201/0774* (2013.01); *B31F 2201/0797* (2013.01); *D21H 27/02* (2013.01); *D21H 27/40* (2013.01); *Y10T 428/24628* (2015.01); *Y10T 428/24694* (2015.01)

(56) References Cited

U.S. PATENT DOCUMENTS

| | | | |
|---|---|---|---|
| 2,404,758 A | | 7/1946 | Teague et al. |
| 2,512,310 A | * | 6/1950 | Corson .............. A47G 27/0231 15/215 |
| 2,633,441 A | | 3/1953 | Buttress |
| 2,669,208 A | | 1/1955 | Schur |
| 2,748,863 A | | 6/1956 | Benton |
| 2,924,863 A | | 2/1960 | Chavannes |
| 3,017,304 A | | 1/1962 | Burgeni |
| 3,034,180 A | | 5/1962 | Greiner et al. |
| 3,073,304 A | | 1/1963 | Schaar |
| 3,081,500 A | | 3/1963 | Griswold et al. |
| 3,081,512 A | | 3/1963 | Griswold |
| 3,097,787 A | | 7/1963 | Schur |
| 3,137,893 A | | 6/1964 | Gelpke |
| 3,222,697 A | * | 12/1965 | Scheermesser ...... A47C 27/144 297/452.48 |
| 3,243,488 A | | 3/1966 | Hannauer, Jr. et al. |
| 3,355,974 A | | 12/1967 | Carmichael |
| 3,466,358 A | | 9/1969 | Muller |
| 3,496,259 A | | 2/1970 | Guenther |
| 3,509,007 A | | 4/1970 | Kalwaites |
| 3,511,740 A | | 5/1970 | Sanders |
| 3,539,423 A | | 11/1970 | Simison et al. |
| 3,542,634 A | | 11/1970 | Such et al. |
| 3,549,742 A | * | 12/1970 | Benz .................... D21F 11/008 139/425 A |
| 3,566,726 A | | 3/1971 | Politis |
| 3,579,763 A | | 5/1971 | Sommer |
| 3,600,361 A | | 8/1971 | Heacock et al. |
| 3,681,182 A | | 8/1972 | Kalwaites |
| 3,681,183 A | | 8/1972 | Kalwaites |
| 3,684,284 A | | 8/1972 | Tranfield |
| 3,695,270 A | | 10/1972 | Dostal |
| 3,718,059 A | | 2/1973 | Clayton |
| 3,760,671 A | | 9/1973 | Jenkins |
| 3,881,987 A | | 5/1975 | Benz |
| 3,911,187 A | | 10/1975 | Raley |
| 3,949,127 A | | 4/1976 | Ostermeier et al. |
| 3,965,906 A | | 6/1976 | Karami |
| 3,994,771 A | | 11/1976 | Morgan, Jr. et al. |
| 4,035,881 A | | 7/1977 | Zocher |
| 4,042,453 A | | 8/1977 | Conway |
| 4,135,021 A | | 1/1979 | Patchell et al. |
| 4,189,344 A | | 2/1980 | Busker |
| 4,211,743 A | | 7/1980 | Nauta et al. |
| 4,244,683 A | | 1/1981 | Rowland |
| 4,276,336 A | | 6/1981 | Sabee |
| 4,300,981 A | | 11/1981 | Carstens |
| 4,343,848 A | | 8/1982 | Leonard, Jr. |
| 4,379,799 A | | 4/1983 | Holmes |
| 4,397,644 A | | 8/1983 | Matthews et al. |
| 4,422,837 A | | 12/1983 | Rasmussen |
| 4,465,726 A | | 8/1984 | Holmes |
| 4,469,734 A | | 9/1984 | Minto et al. |
| 4,514,345 A | | 4/1985 | Johnson et al. |
| 4,528,239 A | | 7/1985 | Trokhan |
| 4,529,480 A | | 7/1985 | Trokhan |
| 4,588,630 A | | 5/1986 | Shimalla |
| 4,609,518 A | | 9/1986 | Curro et al. |
| 4,614,679 A | | 9/1986 | Farrington, Jr. et al. |
| 4,741,941 A | | 5/1988 | Englebert et al. |
| 4,758,297 A | | 7/1988 | Calligarich |
| 4,781,962 A | | 11/1988 | Zamarripa et al. |
| 4,798,604 A | | 1/1989 | Carter |
| 4,816,316 A | * | 3/1989 | Robbins, III ....... B29C 47/0021 428/161 |
| 4,820,294 A | | 4/1989 | Morris |
| 4,840,829 A | | 6/1989 | Suzuki et al. |
| 4,842,794 A | | 6/1989 | Hovis et al. |
| 4,859,519 A | | 8/1989 | Cabe, Jr. et al. |
| 4,886,632 A | | 12/1989 | Van Iten et al. |
| 4,935,087 A | | 6/1990 | Gilman |
| 4,953,270 A | | 9/1990 | Gilpatrick |
| 4,992,324 A | | 2/1991 | Dube |
| 5,019,062 A | | 5/1991 | Ryan et al. |
| 5,062,418 A | | 11/1991 | Dyer |
| 5,143,679 A | | 9/1992 | Weber et al. |
| 5,144,730 A | | 9/1992 | Dilo |
| 5,165,979 A | | 11/1992 | Watkins et al. |
| 5,171,238 A | | 12/1992 | Kajander |
| 5,180,620 A | | 1/1993 | Mende |
| 5,188,625 A | | 2/1993 | Van Iten et al. |
| 5,223,319 A | | 6/1993 | Cotton et al. |
| 5,242,435 A | | 9/1993 | Murji et al. |
| 5,242,632 A | | 9/1993 | Mende |
| 5,328,565 A | | 7/1994 | Rasch et al. |
| 5,382,245 A | | 1/1995 | Thompson |
| 5,383,870 A | | 1/1995 | Takai et al. |
| 5,387,209 A | | 2/1995 | Yamamoto et al. |
| 5,387,385 A | | 2/1995 | Murji et al. |
| 5,405,675 A | | 4/1995 | Sawka et al. |
| 5,414,914 A | * | 5/1995 | Suzuki .................. D04H 18/04 156/168 |
| 5,415,640 A | | 5/1995 | Kirby et al. |
| 5,429,854 A | | 7/1995 | Currie et al. |
| 5,437,653 A | | 8/1995 | Gilman et al. |
| 5,470,326 A | | 11/1995 | Dabi et al. |
| 5,503,715 A | | 4/1996 | Trokhan et al. |
| 5,505,720 A | | 4/1996 | Walters et al. |
| 5,508,080 A | | 4/1996 | Sorimachi et al. |
| 5,518,801 A | | 5/1996 | Chappell et al. |
| 5,533,991 A | | 7/1996 | Kirby et al. |
| 5,534,326 A | | 7/1996 | Trokhan et al. |
| 5,554,145 A | | 9/1996 | Roe |
| 5,560,794 A | | 10/1996 | Currie et al. |
| 5,562,645 A | | 10/1996 | Tanzer et al. |
| 5,567,501 A | | 10/1996 | Srinivasan et al. |
| D375,844 S | | 11/1996 | Edwards et al. |
| 5,573,719 A | | 11/1996 | Fitting |
| 5,575,874 A | | 11/1996 | Griesbach, III et al. |
| 5,580,418 A | | 12/1996 | Alikhan |
| 5,599,420 A | | 2/1997 | Yeo et al. |
| 5,624,427 A | | 4/1997 | Dreier et al. |
| 5,626,571 A | | 5/1997 | Young et al. |
| 5,628,097 A | | 5/1997 | Benson et al. |
| 5,634,915 A | | 6/1997 | Osterdahl |
| 5,637,194 A | | 6/1997 | Ampulski et al. |
| 5,648,142 A | | 7/1997 | Phillips |
| 5,656,119 A | | 8/1997 | Srinivasan et al. |
| 5,658,639 A | | 8/1997 | Curro et al. |
| 5,667,619 A | | 9/1997 | Alikhan |
| 5,667,625 A | | 9/1997 | Alikhan |
| 5,691,035 A | | 11/1997 | Chappell et al. |
| 5,700,255 A | | 12/1997 | Curro |

(56) References Cited

U.S. PATENT DOCUMENTS

| | | | |
|---|---|---|---|
| 5,704,101 A | 1/1998 | Majors et al. |
| 5,709,829 A | 1/1998 | Giacometti |
| 5,714,041 A | 2/1998 | Ayers et al. |
| 5,714,107 A | 2/1998 | Levy et al. |
| 5,723,087 A | 3/1998 | Chappell et al. |
| 5,727,458 A | 3/1998 | Schulz |
| 5,743,776 A | 4/1998 | Igaue |
| 5,743,999 A | 4/1998 | Kamps et al. |
| 5,779,965 A | 7/1998 | Bueuther et al. |
| 5,783,014 A | 7/1998 | Biagioli et al. |
| 5,804,021 A | 9/1998 | Abuto et al. |
| 5,814,389 A | 9/1998 | Giacometti |
| 5,817,394 A | 10/1998 | Alikhan et al. |
| 5,841,107 A | 11/1998 | Riva |
| 5,846,636 A | 12/1998 | Ruppel et al. |
| 5,858,504 A | 1/1999 | Fitting |
| 5,879,494 A | 3/1999 | Hoff et al. |
| 5,891,544 A | 4/1999 | Chappell et al. |
| 5,895,623 A | 4/1999 | Trokhan et al. |
| 5,897,930 A | 4/1999 | Calhoun et al. |
| 5,900,122 A | 5/1999 | Huston |
| 5,906,710 A | 5/1999 | Trokhan |
| 5,914,084 A | 6/1999 | Benson et al. |
| 5,916,507 A | 6/1999 | Dabi et al. |
| 5,916,661 A | 6/1999 | Benson et al. |
| 5,916,663 A | 6/1999 | Chappell et al. |
| 5,919,177 A | 7/1999 | Georger et al. |
| 5,925,026 A | 7/1999 | Arteman et al. |
| 5,925,299 A | 7/1999 | Dierckes et al. |
| 5,935,381 A | 8/1999 | Trokhan et al. |
| 5,964,742 A | 10/1999 | McCormack et al. |
| 5,968,029 A | 10/1999 | Chappell |
| 5,986,167 A | 11/1999 | Arteman et al. |
| 5,993,432 A | 11/1999 | Lodge et al. |
| 5,998,696 A | 12/1999 | Schone |
| 6,007,468 A | 12/1999 | Giacometti |
| 6,025,050 A | 2/2000 | Srinivasan et al. |
| 6,027,483 A | 2/2000 | Chappell et al. |
| 6,030,690 A * | 2/2000 | McNeil | B31F 1/07 156/209 |
| 6,039,555 A | 3/2000 | Tsuji et al. |
| 6,053,232 A | 4/2000 | Biagotti |
| 6,074,524 A | 6/2000 | Wu et al. |
| 6,080,276 A | 6/2000 | Burgess |
| 6,096,016 A | 8/2000 | Tsuji et al. |
| 6,106,928 A | 8/2000 | Laurent et al. |
| 6,109,326 A | 8/2000 | Leakey et al. |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,136,146 A | 10/2000 | Phan et al. |
| 6,155,083 A | 12/2000 | Goeser et al. |
| 6,168,849 B1 | 1/2001 | Braverman et al. |
| 6,176,954 B1 | 1/2001 | Tsuji et al. |
| 6,247,914 B1 | 6/2001 | Lindquist et al. |
| D444,631 S | 7/2001 | Woodbridge et al. |
| 6,261,666 B1 * | 7/2001 | Enderby | B31F 1/07 156/209 |
| 6,264,872 B1 | 7/2001 | Majors et al. |
| 6,287,407 B1 | 9/2001 | Stein et al. |
| 6,296,737 B1 | 10/2001 | Wu et al. |
| 6,324,738 B1 | 12/2001 | Fleissner et al. |
| 6,332,955 B1 | 12/2001 | Meschenmoser |
| 6,344,109 B1 | 2/2002 | Gross |
| 6,344,111 B1 | 2/2002 | Wilhelm |
| 6,355,200 B1 | 3/2002 | Schmidt et al. |
| 6,361,601 B1 | 3/2002 | Schulz |
| 6,368,539 B1 | 4/2002 | Greenfield et al. |
| 6,383,431 B1 | 5/2002 | Dobrin et al. |
| 6,383,441 B1 | 5/2002 | Takai et al. |
| 6,395,122 B1 | 5/2002 | Hisanaka et al. |
| 6,395,211 B1 | 5/2002 | Dettmer et al. |
| 6,395,957 B1 | 5/2002 | Chen et al. |
| 6,398,895 B1 | 6/2002 | Stein et al. |
| 6,410,823 B1 | 6/2002 | Daley et al. |
| 6,420,625 B1 | 7/2002 | Jones et al. |
| 6,423,884 B1 | 7/2002 | Oehmen |
| 6,444,089 B1 | 9/2002 | Hollmark et al. |
| 6,451,718 B1 | 9/2002 | Yamada et al. |
| 6,452,064 B1 | 9/2002 | Thoren et al. |
| 6,454,905 B1 | 9/2002 | Hollmark et al. |
| 6,458,447 B1 | 10/2002 | Cabell |
| 6,464,831 B1 | 10/2002 | Trokhan et al. |
| D466,702 S | 12/2002 | Carlson et al. |
| 6,503,370 B2 | 1/2003 | Hollmark et al. |
| 6,506,329 B1 | 1/2003 | Curro et al. |
| 6,533,898 B2 | 3/2003 | Gross |
| 6,537,936 B1 | 3/2003 | Busam et al. |
| 6,596,127 B2 | 7/2003 | Hollmark et al. |
| 6,610,904 B1 | 8/2003 | Thomas et al. |
| 6,620,485 B1 | 9/2003 | Benson et al. |
| 6,632,504 B1 | 10/2003 | Gillespie et al. |
| D481,872 S | 11/2003 | Hennel et al. |
| 6,647,549 B2 | 11/2003 | McDevitt et al. |
| 6,669,878 B2 | 12/2003 | Yamada et al. |
| 6,716,498 B2 | 4/2004 | Curro et al. |
| 6,726,870 B1 | 4/2004 | Benson et al. |
| 6,736,916 B2 | 5/2004 | Steinke et al. |
| 6,739,024 B1 | 5/2004 | Wagner |
| 6,755,928 B1 | 6/2004 | Biagiotti |
| 6,787,000 B2 | 9/2004 | Burazin et al. |
| 6,794,626 B2 | 9/2004 | Copat et al. |
| 6,808,791 B2 | 10/2004 | Curro et al. |
| 6,811,652 B2 | 11/2004 | Hollmark |
| 6,818,101 B2 | 11/2004 | Vinson et al. |
| 6,818,802 B2 | 11/2004 | Takai et al. |
| 6,830,800 B2 | 12/2004 | Curro et al. |
| 6,837,956 B2 | 1/2005 | Cowell et al. |
| 6,855,220 B2 | 2/2005 | Wildeman |
| 6,863,960 B2 | 3/2005 | Curro et al. |
| 6,872,274 B2 | 3/2005 | Kauschke et al. |
| 6,884,494 B1 | 4/2005 | Curro et al. |
| 6,916,438 B2 | 7/2005 | Berry |
| 6,916,969 B1 * | 7/2005 | Helmfridsson | B32B 7/04 604/366 |
| 6,989,075 B1 | 1/2006 | Kao et al. |
| 6,991,706 B2 | 1/2006 | Lindsay et al. |
| 7,005,558 B2 | 2/2006 | Johansson et al. |
| 7,037,569 B2 | 5/2006 | Curro et al. |
| 7,060,344 B2 * | 6/2006 | Pourdeyhimi | B32B 5/02 428/175 |
| 7,112,257 B2 | 9/2006 | Baggot et al. |
| 7,147,453 B2 | 12/2006 | Boegli |
| 7,175,412 B2 | 2/2007 | Lin |
| 7,229,681 B2 | 6/2007 | Boegli |
| 7,232,613 B2 | 6/2007 | Nakagawa et al. |
| 7,323,072 B2 | 1/2008 | Engelhart et al. |
| 7,399,378 B2 | 7/2008 | Edwards et al. |
| 7,410,683 B2 | 8/2008 | Curro et al. |
| 7,413,630 B2 | 8/2008 | Graff et al. |
| 7,423,003 B2 | 9/2008 | Volpenhein et al. |
| 7,459,180 B2 | 12/2008 | Hamdar et al. |
| 7,497,926 B2 | 3/2009 | Hermans et al. |
| 7,521,588 B2 | 4/2009 | Stone et al. |
| 7,527,615 B2 | 5/2009 | Roe et al. |
| 7,553,532 B2 | 6/2009 | Turner et al. |
| 7,599,378 B1 | 10/2009 | Mecklin |
| 7,632,979 B2 | 12/2009 | Fujii et al. |
| 7,648,752 B2 | 1/2010 | Hoying et al. |
| 7,682,686 B2 | 3/2010 | Curro et al. |
| 7,683,686 B2 | 3/2010 | Curro et al. |
| 7,732,657 B2 | 6/2010 | Hammons et al. |
| 7,754,312 B2 | 7/2010 | Nakajima et al. |
| 7,758,947 B2 | 7/2010 | Maschino et al. |
| 7,799,176 B2 | 9/2010 | Schulz |
| 7,811,665 B2 | 10/2010 | Manifold |
| 7,820,874 B2 | 10/2010 | Manifold |
| 7,901,758 B2 | 3/2011 | Rasmussen |
| 7,939,168 B2 | 5/2011 | Manifold |
| 7,960,020 B2 | 6/2011 | Manifold |
| 7,967,801 B2 | 6/2011 | Hammons |
| 7,989,058 B2 | 8/2011 | Manifold |
| 7,993,317 B2 | 8/2011 | Hammons et al. |

(56) References Cited

U.S. PATENT DOCUMENTS

| | | |
|---|---|---|
| 8,012,309 B2 | 9/2011 | Pare et al. |
| 8,021,591 B2 | 9/2011 | Curro et al. |
| 8,025,966 B2 | 9/2011 | Manifold |
| 8,058,501 B2 | 11/2011 | Hammons |
| 8,158,043 B2 | 3/2012 | Gibson |
| 8,152,957 B2 | 4/2012 | Edwards et al. |
| 8,231,377 B2 | 7/2012 | Abed et al. |
| 8,241,543 B2 | 8/2012 | O'Donnell et al. |
| 8,557,167 B2 | 10/2013 | Kanemasu et al. |
| 8,557,169 B2 | 10/2013 | Stone et al. |
| 8,657,596 B2 | 2/2014 | Lake et al. |
| 8,847,002 B2 | 9/2014 | Goh et al. |
| 9,067,357 B2 | 6/2015 | Orr et al. |
| 9,120,268 B2 | 9/2015 | Lake et al. |
| 9,242,406 B2 | 1/2016 | Coe et al. |
| 9,415,538 B2 | 8/2016 | Mullane |
| 9,623,602 B2 | 4/2017 | Mullane |
| 2001/0029141 A1 | 10/2001 | Mizutami et al. |
| 2002/0016122 A1 | 2/2002 | Curro et al. |
| 2002/0039867 A1 | 4/2002 | Curro et al. |
| 2002/0055310 A1 | 5/2002 | Falk et al. |
| 2002/0103469 A1 | 8/2002 | Chen et al. |
| 2002/0105110 A1 | 8/2002 | Dobrin et al. |
| 2002/0107495 A1 | 8/2002 | Chen et al. |
| 2002/0119720 A1 | 8/2002 | Arora et al. |
| 2002/0132544 A1 | 9/2002 | Takagaki |
| 2003/0021951 A1 | 1/2003 | Desai et al. |
| 2003/0028165 A1 | 2/2003 | Curro et al. |
| 2003/0085213 A1 | 5/2003 | Burckhardt et al. |
| 2003/0121350 A1 | 7/2003 | Hvittfeldt et al. |
| 2003/0121380 A1 | 7/2003 | Cowell et al. |
| 2003/0191442 A1 | 10/2003 | Bewick-Sonntag |
| 2003/0191443 A1 | 10/2003 | Taylor |
| 2003/0204175 A1 | 10/2003 | Mahoney et al. |
| 2003/0204178 A1 | 10/2003 | Febo et al. |
| 2003/0228445 A1 | 12/2003 | Vaughn et al. |
| 2004/0110442 A1 | 6/2004 | Rhim et al. |
| 2004/0121686 A1 | 6/2004 | Wong et al. |
| 2004/0122396 A1 | 6/2004 | Maldonado et al. |
| 2004/0126531 A1 | 7/2004 | Harvey et al. |
| 2004/0131820 A1 | 7/2004 | Turner et al. |
| 2004/0137200 A1 | 7/2004 | Chhabra et al. |
| 2004/0140047 A1 | 7/2004 | Sato et al. |
| 2004/0151796 A1 | 8/2004 | Boegli |
| 2004/0157036 A1 | 8/2004 | Provost et al. |
| 2004/0161556 A1 | 8/2004 | Nishijima |
| 2004/0161586 A1 | 8/2004 | Cree et al. |
| 2004/0229008 A1 | 11/2004 | Hoying et al. |
| 2004/0242097 A1 | 12/2004 | Hasenoehrl et al. |
| 2004/0265533 A1 | 12/2004 | Hoying et al. |
| 2004/0265534 A1 | 12/2004 | Curro et al. |
| 2005/0021753 A1 | 1/2005 | Coleman |
| 2005/0051290 A1 | 3/2005 | Beasley et al. |
| 2005/0064136 A1 | 3/2005 | Turner et al. |
| 2005/0096614 A1 | 5/2005 | Perez et al. |
| 2005/0123726 A1 | 6/2005 | Broering et al. |
| 2005/0153100 A1 | 7/2005 | Zoller et al. |
| 2005/0173055 A1 | 8/2005 | Okuda |
| 2005/0173085 A1 | 8/2005 | Schulz |
| 2005/0217509 A1 | 10/2005 | Covington et al. |
| 2005/0221535 A1 | 10/2005 | Kweon et al. |
| 2005/0221539 A1 | 10/2005 | Kim et al. |
| 2005/0221541 A1 | 10/2005 | Metzler et al. |
| 2005/0221542 A1 | 10/2005 | Yamazaki et al. |
| 2005/0279147 A1 | 12/2005 | Boegli |
| 2005/0283129 A1 | 12/2005 | Hammons et al. |
| 2006/0019056 A1 | 1/2006 | Turner et al. |
| 2006/0063454 A1 | 3/2006 | Chung et al. |
| 2006/0087053 A1 | 4/2006 | Odonnell et al. |
| 2006/0151914 A1 | 7/2006 | Gerndt et al. |
| 2006/0194027 A1 | 8/2006 | Pourdeyhimi et al. |
| 2006/0206072 A1 | 9/2006 | Malakouti et al. |
| 2006/0243367 A1 | 11/2006 | Engelhart et al. |
| 2006/0256343 A1 | 11/2006 | Choma et al. |
| 2006/0286343 A1 | 12/2006 | Curro et al. |
| 2007/0001270 A1 | 1/2007 | Sukegawa et al. |
| 2007/0029694 A1 | 2/2007 | Cree et al. |
| 2007/0131368 A1 | 6/2007 | Xia |
| 2007/0289701 A1 | 12/2007 | Boegli |
| 2008/0116610 A1 | 5/2008 | Boegli |
| 2008/0217809 A1 | 9/2008 | Zhao et al. |
| 2008/0221538 A1 | 9/2008 | Zhao et al. |
| 2008/0221539 A1 | 9/2008 | Zhao et al. |
| 2008/0221541 A1 | 9/2008 | Lavash et al. |
| 2008/0221542 A1 | 9/2008 | Zhao et al. |
| 2008/0224351 A1 | 9/2008 | Curro et al. |
| 2009/0026651 A1 | 1/2009 | Lee et al. |
| 2009/0029106 A1 | 1/2009 | Mauler et al. |
| 2009/0258191 A1 | 10/2009 | Peacock |
| 2010/0001434 A1 | 1/2010 | Atkin |
| 2010/0032867 A1 | 2/2010 | Schmidt |
| 2010/0318047 A1 | 2/2010 | Ducker et al. |
| 2010/0201024 A1 | 8/2010 | Gibson et al. |
| 2010/0233427 A1* | 9/2010 | De Giuseppe ........... B32B 3/30 428/119 |
| 2011/0024940 A1 | 2/2011 | Qureshi et al. |
| 2011/0088859 A1 | 4/2011 | Hultcrantz et al. |
| 2012/0049404 A1 | 3/2012 | Gibson |
| 2012/0059343 A1 | 3/2012 | Kume et al. |
| 2012/0064280 A1 | 3/2012 | Hammons et al. |
| 2012/0064298 A1 | 3/2012 | Orr et al. |
| 2012/0273146 A1 | 11/2012 | Curro et al. |
| 2012/0273148 A1 | 11/2012 | Orr et al. |
| 2012/0273990 A1 | 11/2012 | O'Donnell et al. |
| 2012/0273997 A1 | 11/2012 | Stone et al. |
| 2012/0276238 A1 | 11/2012 | Strube et al. |
| 2012/0276239 A1 | 11/2012 | Coe et al. |
| 2012/0276331 A1 | 11/2012 | Orr et al. |
| 2012/0276337 A1 | 11/2012 | Curro et al. |
| 2012/0276341 A1 | 11/2012 | Lake et al. |
| 2012/0277393 A1 | 11/2012 | Curro et al. |
| 2012/0277701 A1 | 11/2012 | Stone et al. |
| 2012/0277704 A1 | 11/2012 | Marinelli et al. |
| 2012/0277705 A1 | 11/2012 | Marinelli et al. |
| 2012/0277706 A1 | 11/2012 | Marinelli et al. |
| 2012/0277707 A1 | 11/2012 | Orr et al. |
| 2012/0277709 A1 | 11/2012 | Marinelli et al. |
| 2012/0277710 A1 | 11/2012 | Marinelli et al. |
| 2012/0282436 A1 | 11/2012 | Coe et al. |
| 2012/0295060 A1 | 11/2012 | Mullane |
| 2013/0158497 A1 | 6/2013 | Yamaguchi et al. |
| 2014/0225308 A1 | 8/2014 | Okuda et al. |
| 2014/0296815 A1 | 10/2014 | Takken et al. |
| 2014/0336605 A1 | 11/2014 | Hardie et al. |
| 2014/0336608 A1 | 11/2014 | Hao et al. |
| 2015/0038933 A1 | 2/2015 | Day et al. |
| 2015/0167215 A1 | 6/2015 | Mannenin |
| 2015/0250662 A1 | 9/2015 | Isele et al. |
| 2015/0282686 A1 | 10/2015 | Hayase et al. |
| 2015/0321414 A1 | 11/2015 | Lake et al. |

FOREIGN PATENT DOCUMENTS

| | | |
|---|---|---|
| CN | 103417337 | 12/2013 |
| CN | 103417338 | 12/2013 |
| EP | 0494112 A2 | 7/1992 |
| EP | 0598970 A1 | 6/1994 |
| EP | 0 509 012 B1 | 7/1995 |
| EP | 0 955 159 A1 | 11/1999 |
| EP | 0 963 747 A1 | 12/1999 |
| EP | 1 004 412 A1 | 5/2000 |
| EP | 1216818 | 6/2002 |
| EP | 1440197 B1 | 1/2005 |
| EP | 2034072 | 3/2009 |
| FR | 1302937 A | 9/1962 |
| JP | 2006175689 | 7/1992 |
| JP | 2741816 B2 | 4/1998 |
| JP | A-2002-544019 | 12/2002 |
| JP | A 2006-175689 | 7/2006 |
| JP | H04187146 | 7/2006 |
| JP | 3880502 | 2/2007 |
| JP | 3886466 | 2/2007 |
| JP | A-2007-083667 | 4/2007 |
| JP | 4338327 B2 | 10/2009 |

(56) References Cited

FOREIGN PATENT DOCUMENTS

| | | |
|---|---|---|
| JP | 4540590 | 9/2010 |
| JP | 4627035 | 2/2011 |
| JP | 4928181 | 5/2012 |
| WO | WO 92/15445 | 9/1992 |
| WO | WO 95/15138 | 6/1995 |
| WO | WO 02/100632 A1 | 12/2002 |
| WO | WO-2004/108037 A1 | 3/2004 |
| WO | WO 2004/054793 | 7/2004 |
| WO | WO 2005/011936 A1 | 2/2005 |
| WO | WO-2007/001270 A1 | 1/2007 |
| WO | WO-2008/107846 A1 | 9/2008 |
| WO | WO-2010/135503 A1 | 11/2010 |
| WO | WO 2013/047865 | 4/2013 |
| WO | WO 2015/98373 | 7/2015 |
| WO | WO 2015/143772 | 10/2015 |

OTHER PUBLICATIONS

U.S. Appl. No. 13/568,180, filed Aug. 7, 2012, Mullane.
U.S. Appl. No. 13/094,265, filed Apr. 26, 2011, Luigi Marinelli et al.
U.S. Appl. No. 13/455,185, filed Apr. 25, 2012, Luigi Marinelli et al.
U.S. Appl. No. 13/094,279, filed Apr. 26, 2011, Luigi Marinelli et al.
U.S. Appl. No. 13/455,190, filed Apr. 25, 2012, Luigi Marinelli et al.
U.S. Appl. No. 13/094,295, filed Apr. 26, 2011, Luigi Marinelli et al.
U.S. Appl. No. 13/455,194, filed Apr. 25, 2012, Luigi Marinelli et al.
U.S. Appl. No. 13/094,310, filed Apr. 26, 2011, Jill Marlene Orr et al.
U.S. Appl. No. 13/455,199, filed Apr. 25, 2012, Jill Marlene Orr et al.
U.S. Appl. No. 13/094,185, filed Apr. 26, 2011, John Lee Hammons et al.
U.S. Appl. No. 13/094,206, filed Apr. 26, 2011, Jill Marlene Orr et al.
U.S. Appl. No. 13/094,219, filed Apr. 26, 2011, John Brian Strube et al.
U.S. Appl. No. 13/094,477, filed Apr. 26, 2011, Keith Joseph Stone et al.
U.S. Appl. No. 13/094,559, filed Apr. 26, 2011, Richard George Coe et al.
U.S. Appl. No. 13/094,593, filed Apr. 26, 2011, Keith Joseph Stone et al.
U.S. Appl. No. 13/455,508, filed Apr. 25, 2012, John Joseph Curro et al.
U.S. Appl. No. 13/455,532, filed Apr. 25, 2012, John Joseph Curro et al.
U.S. Appl. No. 13/455,698, filed Apr. 25, 2012, John Joseph Curro et al.
U.S. Appl. No. 13/455,857, filed Apr. 25, 2012, Richard George Coe et al.
U.S. Appl. No. 13/455,925, filed Apr. 25, 2012, Jill Marlene Orr et al.
International Search Report dated Sep. 24, 2012, 11 pages.
International Search Report dated Jul. 4, 2012, 12 pages.
International Search Report dated Aug. 8, 2012, 10 pages.
International Search Report dated Aug. 13, 2012, 10 pages.
All Office Actions, U.S. Appl. No. 13/094,206.
All Office Actions, U.S. Appl. No. 13/094,219.
All Office Actions, U.S. Appl. No. 13/094,185.
All Office Actions, U.S. Appl. No. 13/094,195.
All Office Actions, U.S. Appl. No. 14/147,615.
All Office Actions, U.S. Appl. No. 14/271,668.
All Office Actions, U.S. Appl. No. 14/957,673.
All Office Actions, U.S. Appl. No. 15/206,396.

* cited by examiner

METHOD AND APPARATUS FOR DEFORMING A WEB

FIELD OF THE INVENTION

The present invention is directed to deformed web materials and apparatuses and methods for deforming a web to create such materials.

BACKGROUND OF THE INVENTION

Various methods and apparatuses for deforming webs are disclosed in the patent literature. Patents disclosing such methods include: U.S. Pat. No. 4,189,344, Busker; U.S. Pat. No. 4,276,336, Sabee; U.S. Pat. No. 4,609,518, Curro; U.S. Pat. No. 5,143,679, Weber; U.S. Pat. No. 5,562,645, Tanzer; U.S. Pat. No. 5,743,999, Kamps; U.S. Pat. No. 5,779,965, Beuether, et al.; U.S. Pat. No. 5,998,696, Schone; U.S. Pat. No. 6,332,955, Meschenmoser; U.S. Pat. No. 6,739,024 B1, Wagner; U.S. Patent Application Publication 2004/0110442 A1, Rhim; EP 1 440 197 B1, Thordahl; U.S. Pat. No. 6,916,969, Helmfridsson; U.S. Patent Application Publication No. 2006/0151914 A1, Gemdt; U.S. Pat. No. 7,147,453 B2, Boegli; U.S. Pat. No. 7,423,003, Volpenhein; U.S. Pat. No. 7,323,072 B2, Engelhart, et al.; U.S. Patent Application Publication No. 2006/0063454, Chung; U.S. Patent Application Publication No. 2007/0029694 A1, Cree, et al.; U.S. Patent Application Publication No. 2008/0224351 A1, Curro, et al.; U.S. Patent Application Publication No. 2009/0026651 A1, Lee, et al.; U.S. Pat. No. 7,521,588 B2, Stone, et al.; and U.S. Patent Application Publication No. 2010/0201024 A1, Gibson, et al.

However, the search continues for methods and apparatuses that are capable of forming new structures in webs that provide the webs with additional properties. In the case of webs used in absorbent articles, such new structures may include those that provide a single portion of the web with dual, or more, properties (such as improved softness, fluid handling, or other properties) in a predetermined portion of the web. A need also exists for apparatuses that will allow a web to be deformed multiple times while maintaining control over the registration of the deformations in the web. A further need exists for apparatuses that are capable of deforming a web multiple times with an apparatus that has a small footprint on a manufacturing floor.

SUMMARY OF THE INVENTION

The present invention is directed to deformed web materials and apparatuses and methods for deforming a web to create such materials. Such materials can be provided as components of products such as absorbent articles (such as topsheets, backsheets, acquisition layers, liquid handling layers, absorbent cores), packaging (such as flow wrap, shrink wrap, and polybags), trash bags, food wrap, wipes, facial tissue, toilet tissue, paper towels, and the like. There are numerous non-limiting embodiments of the present invention.

In one non-limiting embodiment, the deformed web material comprises a web having discrete deformations formed therein. The deformations may be features in the form of portions of the web with apertures therein, protrusions, depressed areas, and combinations thereof. These features may extend out from the surface on one side of the web, or from both of the surfaces of the web. Different features may be intermixed with one another.

The apparatuses and methods can, in certain non-limiting embodiments, be configured for deforming a web in a single nip. In one embodiment, the method involves feeding a web into a nip that is formed between two intermeshing rolls. The two rolls are configured for deforming a web with at least two sets of deformations that are oriented in different directions relative to the surfaces of the web.

In other embodiments, the apparatuses and methods can be configured for deforming a web at least two times (that is, in at least two or more nips). In such embodiments, the apparatus may comprise nested, or other arrangements of, multiple rolls in which the web may be maintained substantially in contact with at least one of the rolls throughout the process, and at least two of the rolls define two or more nips thereon with other rolls. In some embodiments, rolls can be used to expose a different side of the web for a subsequent deformation step. In these or other embodiments, the rolls can be used to transfer the web between rolls in such a manner that it may offset the rolls and/or web so that subsequent deformations are formed at a different cross-machine direction alignment than prior deformations. In some cases, this may be used to achieve a tighter spacing between deformations than might otherwise be possible.

BRIEF DESCRIPTION OF THE DRAWINGS

The following detailed description will be more fully understood in view of the drawings in which.

Figure 1:
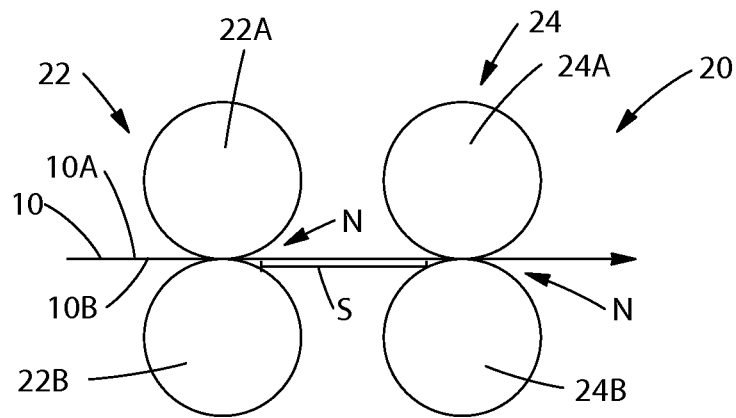
FIG. 1 is a schematic side view of a prior art method and apparatus for deforming a web.

The embodiments shown in the drawings are illustrative in nature and are not intended to be limiting of the invention defined by the claims. Moreover, the features of the invention will be more fully apparent and understood in view of the detailed description.

DETAILED DESCRIPTION

Definitions

The term "absorbent article" includes disposable articles such as sanitary napkins, panty liners, tampons, interlabial devices, wound dressings, diapers, adult incontinence articles, wipes, and the like. Still further, the absorbent members produced by the methods and apparatuses disclosed herein can find utility in other webs such as scouring pads, dry-mop pads (such as SWIFFER® pads), and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet.

The term "absorbent core", as used herein, refers to the component of the absorbent article that is primarily responsible for storing liquids. As such, the absorbent core typically does not include the topsheet or backsheet of the absorbent article.

The term "absorbent member", as used herein, refers to the components of the absorbent article that typically provide one or more liquid handling functionality, e.g., liquid acquisition, liquid distribution, liquid transportation, liquid storage, etc. If the absorbent member comprises an absorbent core component, the absorbent member can comprise the entire absorbent core or only a portion of the absorbent core.

The term "absorbent structure", as used herein, refers to an arrangement of more than one absorbent component of an absorbent article.

The term "adjacent", as used herein, with reference to features or regions, means near or close to, and which need not be in contact with each other.

The term "aperture", as used herein, refers to a hole. The apertures can either be punched cleanly through the web so that the material surrounding the aperture lies in the same plane as the web prior to the formation of the aperture (a "two dimensional" aperture), or holes formed in which at least some of the material surrounding the opening is pushed out of the plane of the web. In the latter case, the apertures may resemble a protrusion or depression with an aperture therein, and may be referred to herein as a "three dimensional" aperture, a subset of apertures.

The term "component" of an absorbent article, as used herein, refers to an individual constituent of an absorbent article, such as a topsheet, acquisition layer, liquid handling layer, absorbent core or layers of absorbent cores, backsheets, and barriers such as barrier layers and barrier cuffs.

The term "cross-machine direction" or "CD" means the path that is perpendicular to the machine direction in the plane of the web.

The term "deformable material", as used herein, is a material which is capable of changing its shape or density in response to applied stresses or strains.

The term "discrete", as used herein, means distinct or unconnected. When the term "discrete" is used relative to forming elements on a forming member, it is meant that the distal (or radially outwardmost) ends of the forming elements are distinct or unconnected in all directions, including in the machine and cross-machine directions (even though bases of the forming elements may be formed into the same surface of a roll, for example).

The term "disposable" is used herein to describe absorbent articles and other products which are not intended to be laundered or otherwise restored or reused as an absorbent article or product (i.e., they are intended to be discarded after use and, preferably, to be recycled, composted or otherwise disposed of in an environmentally compatible manner).

The term "forming elements", as used herein, refers to any elements on the surface of a forming member that are capable of deforming a web. The term "forming elements" includes both continuous or non-discrete forming elements such as the ridges and grooves on ring rolls, and discrete forming elements.

The term "intermixed", as used herein, refers to features that are distributed between other features over at least some portion of the surface of a component, in which the features differ from each other as described herein. The term "intermixed" comprises arrangements of features in which at least two of the closest features in any direction (including, but not limited to longitudinal, transverse, or diagonal) differ from each other as described herein, even though there may be a similar feature that is as close as, or closer to, a given feature in another direction.

The term "Interpenetrating SELF" and the acronym "IPS", as used herein, refers to a process that uses The Procter & Gamble Company's SELF technology (described below) to combine at least two layers or materials together. Tufts may be formed in both materials; or, the tuft of one material may burst through the other material. Interpenetrating SELF is described in greater detail in U.S. Pat. No. 7,648,752.

The term "joined to" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The term "joined to" encompasses configurations in which an element is secured to another element at selected locations, as well as configurations in which an element is completely secured to another element across the entire surface of one of the elements. The term "joined to" includes any known manner in which elements can be secured including, but not limited to mechanical entanglement.

The term "layer" is used herein to refer to an absorbent member whose primary dimension is X-Y, i.e., along its length (or longitudinal direction) and width (or transverse direction). It should be understood that the term "layer" is not necessarily limited to single layers or sheets of material. Thus the layer can comprise laminates or combinations of several sheets or webs of the requisite type of materials. Accordingly, the term "layer" includes the terms "layers" and "layered".

The term "machine direction" or "MD" means the path that material, such as a web, follows through a manufacturing process.

The term "male/female embossing" as used herein, refers to an embossing apparatus and process that involves the use of at least a pair of patterned rolls, wherein the first patterned roll comprises one or more projections or protrusions, and the second patterned roll comprises one or more recesses into which one or more of the projections of the first patterned roll mesh. The projections and recesses may be discrete embossing elements, and they may have matched or unmatched patterns. The term "male/female embossing", thus, excludes embossing processes that utilize the combination of a patterned roll against a flat anvil roll or deformable roll.

The term "macroscopic", as used herein, refers to structural features or elements that are readily visible and distinctly discernable to a human having 20/20 vision when the perpendicular distance between the viewer's eye and the web is about 12 inches (30 cm). Conversely, the term "microscopic" refers to such features that are not readily visible and distinctly discernable under such conditions.

The terms "mechanically impacting" or "mechanically deforming", may be used interchangeably herein, to refer to processes in which a mechanical force is exerted upon a material.

The term "Micro-SELF" is a process that is similar in apparatus and method to that of the SELF process defined herein. Micro-SELF teeth have different dimensions such that they are more conducive to forming tufts with openings on the leading and trailing ends. A process using micro-SELF to form tufts in a web substrate is disclosed in U.S. Patent application Publication No. US 2006/0286343A1.

The term "permanently deformed", as used herein, refers to the state of a deformable material whose shape or density has been permanently altered in response to applied stresses or strains.

The term "post-consumer recycled material" as used herein generally refers to material that can originate from post-consumer sources such as domestic, distribution, retail, industrial, and demolition. "Post-consumer fibers" means fibers obtained from consumer products that have been discarded for disposal or recovery after having completed their intended uses and is intended to be a subset of post consumer recycled materials. Post-consumer materials may be obtained from the sorting of materials from a consumer or manufacturer waste stream prior to disposal. This definition is intended to include materials which are used to transport product to a consumer, including, for example, corrugated cardboard containers.

The terms "ring roll" or "ring rolling" refer to a process using deformation members comprising counter rotating rolls, intermeshing belts or intermeshing plates containing continuous ridges and grooves where intermeshing ridges (or projections) and grooves (or recesses) of deformation members engage and stretch a web interposed therebetween. For ring rolling, the deformation members can be arranged to stretch the web in the cross machine direction or the machine direction depending on the orientation of the ridges and grooves.

The term "rotary knife aperturing" (RKA) refers to a process and apparatus using intermeshing deformation members similar to those described herein with respect to SELF or micro-SELF deformation members. The RKA process differs from SELF or micro-SELF in that the relatively flat, elongated teeth of a SELF or micro-SELF deformation member have been modified to be pyramid shaped, elongated with at least six sides, the sides being substantially triangular and tapered to a point at the distal end. The teeth can be sharpened to cut through as well as deform a web to produce an apertured web, or in some cases, a three-dimensionally apertured web, as disclosed in U.S. Patent Application Publication Nos. US 2005/0064136A1, US 2006/0087053A1, and US 2005/021753. In other respects such as tooth height, tooth spacing, pitch, depth of engagement, and other processing parameters, RKA and the RKA apparatus can be the same as described herein with respect to SELF or micro-SELF.

The terms "SELF" or "SELF'ing", refer to Procter & Gamble technology in which SELF stands for Structural Elastic Like Film. While the process was originally developed for deforming polymer film to have beneficial structural characteristics, it has been found that the SELF'ing process can be used to produce beneficial structures in other materials. Processes, apparatuses, and patterns produced via SELF are illustrated and described in U.S. Pat. Nos. 5,518,801; 5,691,035; 5,723,087; 5,891,544; 5,916,663; 6,027,483; and 7,527,615 B2.

The term "tuft", as used herein, refers to a particular type of protrusion that may be formed in a nonwoven web. Tufts typically have a tunnel-like configuration, and in some cases may be open at one or both of their ends.

The term "upper" refers to absorbent members, such as layers, that are nearer to the wearer of the absorbent article during use, i.e. towards the topsheet of an absorbent article; conversely, the term "lower" refers to absorbent members that are further away from the wearer of the absorbent article towards the backsheet. The term "laterally" corresponds to direction of the shorter dimension of the article, which generally during use corresponds to a left-to-right orientation of the wearer. "Longitudinally" then refers to the direction perpendicular to the lateral one, but not corresponding to the thickness direction.

The term "Z-dimension" refers to the dimension orthogonal to the length and width of the web or article. The Z-dimension usually corresponds to the thickness of the web or article. As used herein, the term "X-Y dimension" refers to the plane orthogonal to the thickness of the web or article. The X-Y dimension usually corresponds to the length and width, respectively, of the web or article.

I. Deformed Web Materials.

The present inventions are directed to deformed web materials and methods and apparatuses for deforming a web. Methods and apparatuses are disclosed that are capable of forming new structures in webs that provide the webs with additional properties. It should be understood that while the term "deformed web materials" is utilized herein, the object is to create components, such as absorbent members (or non-absorbent components), for absorbent articles from such deformed web materials. In such cases, the deformed web materials will be cut into individual components for absorbent articles. The deformed web materials can also be used in products other than absorbent articles including, but not limited to packaging materials and trash bags.

Structures can be provided in webs and the components formed therefrom which are not possible to produce with current methods and tooling (forming components). Such structures include features extending out of the plane of the web on both sides of the web, and/or features that are intermixed between other features. The web can, in some cases, also be provided with features that are more closely spaced than is possible with conventional tooling. In the case of webs used in absorbent articles, such new structures may include those that provide a single portion of the web with dual, or more, properties (such as improved softness, fluid handling, or other properties) in a predetermined portion of the web. The apparatuses and processes can allow a web to be deformed multiple times while maintaining control over the registration of the deformations in the web. That is, the location/registration of the web may be controlled in the machine direction and in the cross-machine direction from the time the web is fed into the first forming nip to the time it exits the last forming nip so deformations made in the downstream nips occur in a controlled location relative to deformations made in previous nips.

The web (or "precursor web") that will be deformed can comprise any suitable deformable material, such as a woven, nonwoven, film, combination, or laminate of any of the foregoing materials. As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing, spunbonding, hydroentangling, airlaid, wet-laid, through-air-dried paper making processes, and bonded carded web processes, including carded thermal bonding. The woven, nonwoven, film, combination, or laminate can be made of any suitable materials including, but not limited to natural materials, synthetic materials, and combinations thereof. Suitable natural materials include, but are not limited to cellulose, cotton linters, bagasse, wool fibers, silk fibers, etc. In some embodiments, the web materials may be substantially free of cellulose, and/or exclude paper materials. In other embodiments, the methods described herein may be performed on cellulose-containing precursor materials. Suitable synthetic materials include, but are not limited to rayon and polymeric materials. Suitable polymeric materials include, but are not limited to: polyethylene, polyester, polyethylene terephthalate (PET), and polypropylene. Any of the materials described above may comprise post-consumer recycled material.

In one non-limiting embodiment, the deformed web material comprises a web having discrete deformations formed therein. The web has a first surface and a second surface. The web comprises: a) substantially undeformed first regions, the undeformed regions having surfaces that correspond to the first and second surfaces of the web prior to the formation of deformations therein; b) a plurality of spaced apart first formed features (or "first features") in first locations comprising features that can comprise: portions of the web material with apertures therein; protrusions; and depressed areas (or "depressions"); and c) a plurality of spaced apart second formed features (or "second features") in second locations comprising features that can comprise: portions of the web material with apertures therein; protrusions; and depressed areas (or "depressions"). In some embodiments, the first features and/or the second features may be selected from the group consisting of one or more of the foregoing types of features. The second features may be of a different type and/or have different properties or characteristics than the first features, and the second features may be intermixed with the first features. In some embodiments, all of the adjacent features, or all of closest features, may be of a different type and/or have different properties. In some embodiments, at least four of the closest eight features in any direction to a given feature may be of a different type and/or have different properties. The web material may further comprise third, fourth or more formed features. The third, fourth, or more features may comprise any of the types of features or have any of the properties described herein, and may differ from the first and second features in any such aspects.

In certain embodiments, it may be possible to densely pack multiple features within a relatively small area. For example, the center-to-center spacing in any direction between a first feature and a second feature may be less than or equal to about 20 mm, alternatively 10 mm, 5 mm, 3 mm, 2 mm, or 1 mm, or lie in any range between two of these numbers. The total number of features in an area that measures 1 square inch (645 mm$^2$) may be greater than or equal to 4, 25, 100, 250, 500, or 645, or lie in any range between two of these numbers. The number of first features in one square inch may be the same or different from the number of the second features in that same area. The number of features in a one inch square area can be determined by marking a square area on the material that measures 1 inch (25.4 mm) by 1 inch with a fine tip pen or marker and counting the number of first, second, third, etc. features that lie fully or partially within and on the boundary of the 1 inch square. A low power microscope or other magnifying aid can be used to aid visibility of the features in the material if needed. The ratio of the number of first features to the number of second features may be between 0.0016 and 155. When the number of first features is the same as the number of second features, the ratio will be 1. For embodiments related to a web comprising a film, the ratio of the number of first features to the number of second features may be between 0.125 and 8. Note, in cases where there are third, fourth or more different types of features, these ratios would apply to all paired combinations of features.

The first features and second features may be of any suitable size. Typically, either the first features or the second features will be macroscopic. In some embodiments, the first features and the second features will both be macroscopic. The plan view area of the individual features may, in some embodiments of the web, be greater than or equal to about 0.5 mm$^2$, 1 mm$^2$, 5 mm$^2$, 10 mm$^2$, or 15 mm$^2$, or lie in any range between two of these numbers. The methods described herein can, however, be used to create first features and/or second features that are microscopic which have plan view areas less than 0.5 mm$^2$.

The first features and second features may be of any suitable configuration. The features may be continuous and/or discrete. Suitable configurations for the features include, but are not limited to: ridges (continuous protrusions) and grooves (continuous depressions); tufts; columnar shapes; dome-shapes, tent-shapes, volcano-shapes; features having plan view configurations including circular, oval, hour-glass shaped, star shaped, polygonal, polygonal with rounded corners, and the like, and combinations thereof. Polygonal shapes include, but are not limited to rectangular (inclusive of square), triangular, hexagonal, or trapezoidal. In some embodiments, the first and/or second features may exclude one or more of the configurations listed above.

The first features and the second features may differ from each other in terms of one or more of the following properties: type, shape, size, aspect ratio, edge-to-edge spacing, height or depth, density, color, surface treatment (e.g., lotion, etc.), number of web layers within the features, and orientation (protruding from different sides of the web). The term "type", as used herein, refers to whether the feature is an aperture (a two dimensional aperture, or a three dimensional aperture), a protrusion (a tuft, or other kind of protrusion), or a depression. Two features will be considered to be different in type if one feature comprises one of these features listed (for example, a two dimensional aperture), and the other feature comprises another one of the listed features (for example, a three dimensional aperture). When the features are described as differing from each other in one of more of the properties listed above, it is meant to include those differences other than minor differences that are the result of variations within manufacturing tolerances. It should also be understood that although the web material may have discrete thermal or adhesive bond sites therein, in some embodiments the features of interest imparted by this process herein do not include such bond sites.

The various types of deformed webs will be shown in conjunction with the descriptions of the apparatuses and methods used to form the same. These webs can be cut to form various components of products such as absorbent articles (such as topsheets, backsheets, acquisition layers, absorbent cores), packaging (such as flow wrap, shrink wrap, and polybags), trash bags, food wrap, wipes, facial tissue, toilet tissue, paper towels, and the like.

II. Apparatuses for Deforming Web Materials.

Prior art approaches are not suitable for creating well-defined inter-mixed features with controlled placement of the features. Therefore, it is desirable to design a process that enables better independent control over the formation of two or more sets of features. Two approaches for achieving better independent control over the formation of each set of features are provided here. One approach utilizes a single nip with two rolls comprising discrete male forming elements wherein at least one roll comprises two or more raised ridges. A second approach comprises a multi-hit (multi-nip) configuration that enables controlled placement and orientation of multiple sets of features. Each of these approaches may enable independent control over the formation of each set of features and better pattern conformation of the web to the roll such that the desired size and/or shape of the feature is achieved.

The mechanical deformation process can be carried out on any suitable apparatus that may comprise any suitable type(s) of forming structure. Suitable types of forming structures include, but are not limited to: a pair of rolls that define a nip therebetween; pairs of plates; belts; etc. Using an apparatus with rolls can be beneficial in the case of continuous processes, particularly those in which the speed of the process is of interest. Although the apparatuses will be described herein for convenience primarily in terms of rolls, it should be understood that the description will be applicable to forming structures that have any other suitable configurations.

To assist in understanding the present inventions, several prior art apparatuses are shown. FIG. 1 shows one embodiment of a prior art apparatus 20 for deforming a web material. The apparatus shown in FIG. 1 will be referred to as a "paired roll arrangement". In this apparatus, a web material 10 is fed through a first nip N between a first pair 22 of stacked rolls comprising rolls 22A and 22B. Downstream from the first pair 22 of stacked rolls, the web is fed through a second nip N between a second pair 24 of stacked rolls comprising rolls 24A and 24B. The web material 10 has a first surface or side 10A and a second surface or side 10B. Typically, such an apparatus is used to form continuous deformations into a web. Applicants have considered utilizing such an apparatus to form discrete deformations into the web 10 at each nip. However, such an apparatus is subject to difficulties in registering or aligning deformations that may be made at the second nip with deformations that are made at the first nip. These difficulties are caused at least in part by the fact that there is a free span of web material, S, between the first and second nips that is not maintained in contact with any rolls. This results in loss of precision in control over the portion of the web that will be deformed at the second nip. This is particularly the case with more flexible or lower modulus materials, as are often found in disposable products that can change dimensions in the free span between successive nips.

Figure 2:
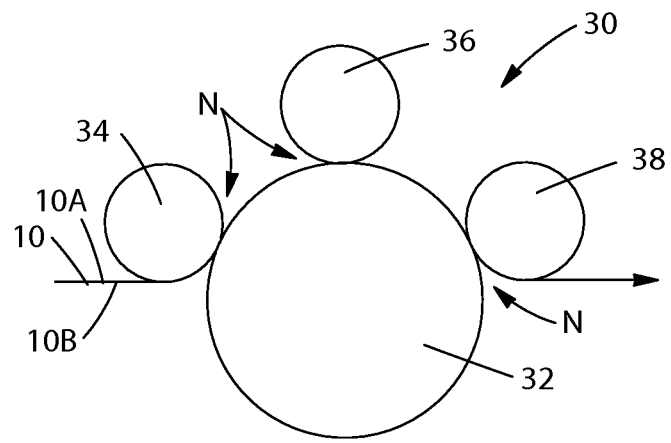
FIG. 2 is a schematic side view of another prior art apparatus for deforming a web.

FIG. 2 shows another prior art apparatus for deforming a web material. The apparatus 30 shown in FIG. 2 will be referred to as a "planetary" or "satellite" roll arrangement. In this apparatus, there is a "sun" or central roll 32, and one or more satellite rolls 34, 36, and 38, that form nips N with the central roll 32. It should be understood, however, that although the apparatuses shown in FIGS. 1 and 2 are known, there are variations of the same disclosed herein that are not believed to be known, and it is expressly not admitted that FIG. 1 or 2 disclose such variations. The disadvantage of a conventional planetary roll arrangement is that the downstream satellite rolls 36 and 38 can only deform the web 10 on the same side as the first satellite roll 34. Thus, it would not ordinarily be possible to form discrete deformations in the web, some of which extend out from one surface of the web, and some of which extend out from another surface of the web with independent control of the deformation and placement of multiple sets of features. Another disadvantage of a conventional planetary roll arrangement is that satellite rolls 34, 36 and 38 are only capable of deforming the web 10 in the recesses of the central roll. Therefore, the spacing of the formed features is limited by the spacing of the recesses on the central roll. Thus, it would not be possible to form discrete deformations in the web that have a smaller center-to-center spacing than the center-to-center spacing of the recesses on the forming roll(s).

Figure 3:
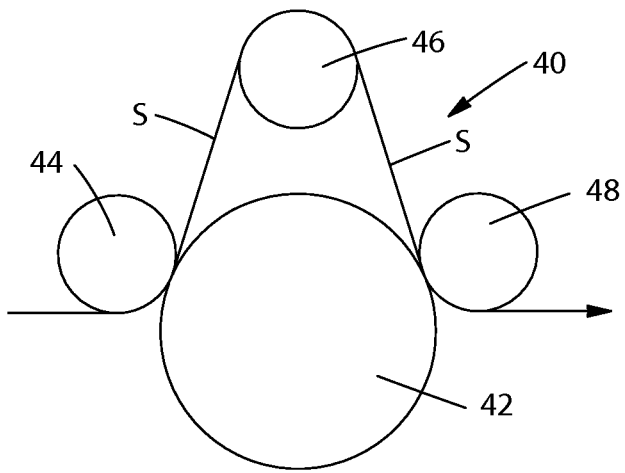
FIG. 3 is a schematic side view of another prior art method and apparatus for deforming a web.

FIG. 3 shows another prior art apparatus for deforming a web material, which is a variation of the apparatus shown in FIG. 2. The apparatus has a central roll 42 and satellite rolls 44 and 48. The apparatus 40 shown in FIG. 3 differs from the apparatus shown in FIG. 2 in that at one place around the central roll 42, the web material 10 is transferred from the surface of the central roll 42 to a roll 46 that is spaced away from the central roll 42 such that this latter roll 46 does not form a nip with the central roll 42. The apparatus shown in FIG. 3 will be referred to as a planetary or satellite roll arrangement with a removable roll. The disadvantage of a planetary or satellite roll arrangement with a removable roll arrangement is that if deformations are being made in the web 10 after the web leaves the central roll 42 to wrap around the removable roll 46, it is difficult to maintain control over the registration of the deformations in the web due to the large free spans of material, S, between the deformation nips.

Applicants have also considered using a single nip comprising two rolls with discrete male forming elements to form multiple set of discrete deformations into the web. The disadvantage of this approach is that typically, one set of features will be preferentially formed over the other, and the second set of features may never be formed or will not result in the desired feature size and/or shape. Without wishing to be bound by any particular theory, it is believed that this is a result of the material following the path of least resistance, which is dependent upon the two mating roll patterns. In situations in which the mating rolls are identical, a conventional single nip apparatus will not produce the same structure that is created if the elements are formed independently in separate nips. Prior art approaches do not provide an apparatus that can create independent control of the deformation and placement of multiple sets of features. Because of the drawbacks associated with the above apparatuses, applicants have developed improved configurations for the arrangement of the rolls.

Figure 4:
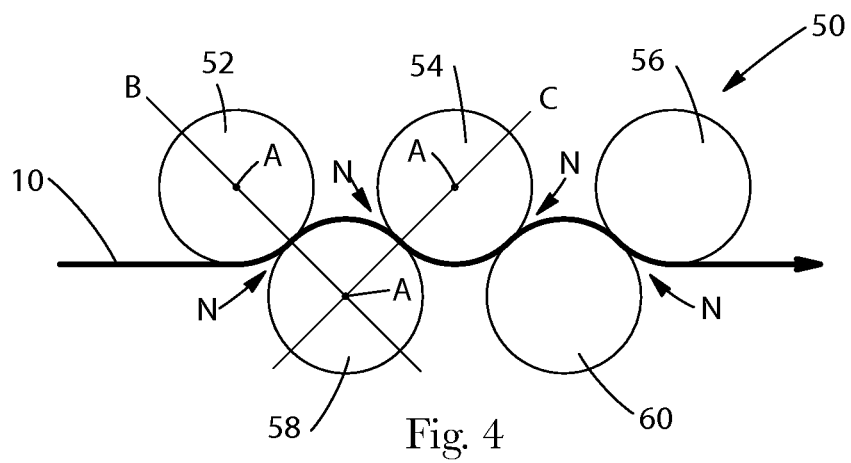
FIG. 4 is a schematic side view of one embodiment of a method and apparatus for deforming a web.

FIG. 4 shows one non-limiting embodiment of an apparatus that can be used in the processes described herein. The apparatus 50 shown in FIG. 4 will be referred to as a "nested roll" arrangement. In this apparatus 50, the rolls 52, 54, 56, 58, and 60 are arranged in an offset configuration when viewed from the side (that is, the ends of the rolls). In this apparatus, at least one roll, such as rolls 54, 58, and 60, are positioned in a gap between two adjacent rolls. At least two of the rolls define two or more nips N thereon with other rolls. For example, roll 58 forms two nips—with rolls 52 and 54; and roll 54 forms two nips—with rolls 58 and 60. Typically, in a nested roll arrangement, there will be at least four generally cylindrical rolls, and at least two of the rolls will have forming elements thereon. More specifically, in a nested configuration, the rolls each have an axis, A, and the rolls are arranged so that if the rolls are viewed from one of their circular sides, and lines B and C are drawn through the axes A of at least two different pairs of said rolls (which pairs may have at least one roll in common), will be non-parallel. As shown in FIG. 4, at least some of the lines B and C drawn through the axes of adjacent pairs of rolls form an angle therebetween.

The nested roll arrangement may provide several advantages. A nested roll arrangement provides more nips per total number of rolls than some of the roll arrangements shown in FIGS. 1-3. The nested roll arrangement maintains control of the web 10 for registering deformations in the web since all portions along the length of the web on at least one surface of the web may remain substantially in contact with at least one of the rolls from the point where the web enters the first forming nip to the location where the web exits the last forming nip. When the web is described as remaining substantially in contact with the rolls, the web may contact the roll(s) only on the tips of the forming elements on the roll, bridging between adjacent forming elements. A web containing small free spans between adjacent forming elements would still be considered to be in substantial contact with the rolls, as would a roll arrangement in which there is an unsupported section of the web or free span that is less than or equal to 2 cm in length. The nested roll arrangement provides the ability to create deformations in different cross-machine direction locations (or lanes) and on different sides of a web. The nested roll arrangement also has a smaller footprint on a manufacturing floor. The entire nested roll arrangement shown in FIG. 4 could also be rotated 90° so that the rolls are stacked vertically, and the apparatus would occupy even less space on a manufacturing floor.

Figure 4A:
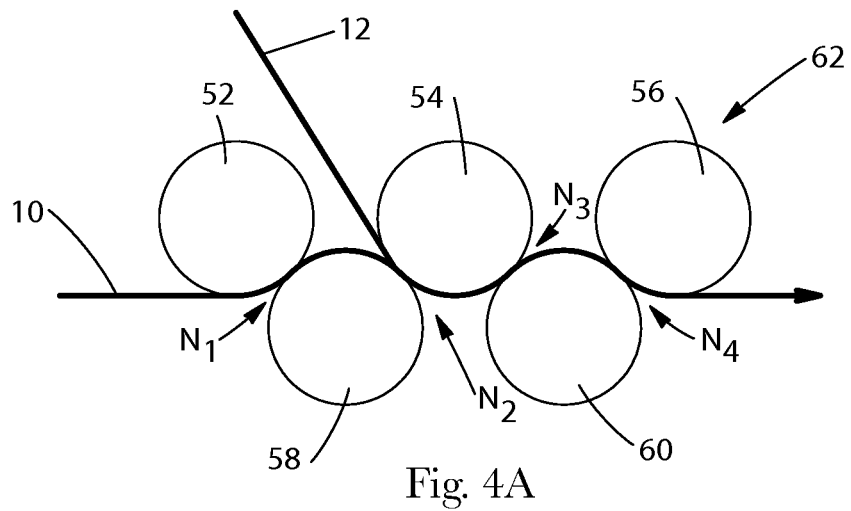
FIG. 4A is a schematic side view of an alternative embodiment of a method and apparatus for deforming a web wherein a second web is introduced at a nip downstream of the first nip.

FIG. 4A shows an alternative embodiment of a method and nested roll apparatus 62 for deforming a web. The apparatus 62 is similar to the apparatus shown in FIG. 4. However, in the embodiment shown in FIG. 4A, a second web 12 is introduced at a nip N2 downstream of the first nip N1. The methods described herein contemplate that any number of additional webs may be fed into the apparatuses at any nip downstream of the first nip. The additional layers may be used to add webs having different chemical compositions, formulations, aesthetics, conductive properties, aromatic properties, and mechanical properties. The processes described herein enable independent control of the features formed in a multi-layer structure, providing additional control over the function and aesthetics of the features. For example, this process could provide the ability to create multi-layer structures where the some features have more layers through their thickness than other features.

The rolls used in the apparatuses and methods described herein are typically generally cylindrical. The term "generally cylindrical", as used herein, encompasses rolls that are not only perfectly cylindrical, but also cylindrical rolls that may have elements on their surface. The term "generally cylindrical" also includes rolls that may have a step-down in diameter, such as on the surface of the roll near the ends of the roll. The rolls are also typically rigid (that is, substantially non-deformable). The term "substantially non-deformable", as used herein, refers to rolls having surfaces (and any elements thereon) that typically do not deform or compress under the conditions used in carrying out the processes described herein. The rolls can be made from any suitable materials including, but not limited to steel, aluminum or rigid plastic. The steel may be made of corrosion resistant and wear resistant steel, such as stainless steel. The rolls may or may not be heated. If heated, consideration of thermal expansion effects must be accommodated according to well known practices to one skilled in the art of thermo-mechanical processes.

The rolls used in the apparatuses and methods described herein are used to mechanically deform portions of the web material or materials. The mechanical deformation process may be used to permanently deform portions of the web and form the types of features in the web described above. The terms "mechanically deform" and "mechanical deformation", as used herein, do not include hydroforming processes. The features formed by the processes described herein may be registered since the processes described herein maintain control of the web, which may be in substantially continuous contact with at least one of the rolls (which serves as a metering surface) between the first nip through which the web material passes until the material exits the last nip.

The rolls may have any suitable type of elements on their surface (or surface configuration). The surface of the individual rolls may, depending on the desired type of mechanical deformation, be provided with forming elements comprising: "male" elements such as discrete projections, or continuous projections such as ridges; "female" elements or recesses such as discrete or continuous voids in the surface of the rolls; or any suitable combination thereof. The female elements may have a bottom surface (which may be referred to as depressions, cavities, or grooves), or they may be in the form of apertures (through holes in the surface of the rolls). In some embodiments, the forming elements on the components (such as the rolls) of the forming structure may comprise the same general type (that is, the opposing components may both have male forming elements thereon, or combinations of male and female elements).

The forming elements may have any suitable shape or configuration. A given forming element can have the same plan view length and width dimensions (such as a forming element with a circular or square shaped plan view). Alternatively, the forming element may have a length that is greater than its width (such as a forming element with a rectangular plan view), in which case, the forming element may have any suitable aspect ratio of its length to its width. Suitable configurations for the forming elements include, but are not limited to: ridges and grooves, teeth having a triangular-shaped side view; columnar shapes; elements having plan view configurations including circular, oval, hour-glass shaped, star shaped, polygonal, and the like, and combinations thereof. Polygonal shapes include, but are not limited to rectangular, triangular, hexagonal, or trapezoidal. The forming elements can have tips that are flat, rounded or sharp. In certain embodiments, the shapes of the female elements may differ from the shapes of any mating male forming elements. In certain embodiments, the female forming elements can be configured to mate with one or more male forming elements.

The forming elements can be of any suitable size and have any suitable spacing. For instance, at least one forming element for forming micro-textured webs has a center-to-center spacing of less than about 800 microns with at least three, at least four, or at least five of its adjacent forming elements as described in U.S. patent application Ser. No. 13/094,477 entitled "Process for Making a Micro-Textured Web", filed on the same date as the present application. In some embodiments, at least 25%, at least 50%, at least 75%, at least 95%, or all of the forming elements on a forming structure have center-to-center spacings of less than about 800 microns with at least three, at least four, or at least five of their adjacent forming elements 10. Other acceptable center-to-center spacings are from about 30 microns to about 700 microns, from about 50 microns to about 600 microns, from about 100 microns to about 500 microns, or from about 150 microns to about 400 microns. The center-to-center spacings among adjacent forming elements may be the same or different. The center-to-center spacing of the forming elements may range from the scale used for such micro-textured webs up to, or greater than, the examples of the size of the center-to-center spacing of the larger forming elements described herein. Suitable configurations for the forming components include, but are not limited to: ring rolls; SELFing rolls; Micro-SELFing rolls; and RKA rolls; male/female embossing rolls; and the forming structures for forming the micro-textured web in the patent application described above. Several such roll surface configurations are described below.

Figure 5:
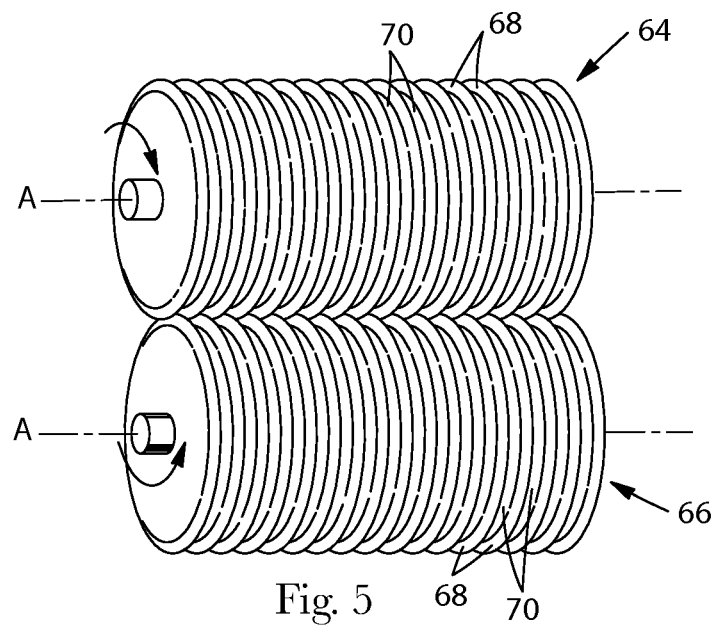
FIG. 5 is an enlarged perspective view of a pair of ring rolls suitable for use in the methods and apparatuses described herein.

FIG. 5 shows an embodiment in which the rolls 64 and 66 are referred to herein as "ring rolls". The rolls 64 and 66, as in the case of the rolls in the other apparatuses shown and described herein, are carried on respective rotatable shafts having their axes A of rotation disposed in a parallel relationship. In all of the embodiments described herein, the rolls are non-contacting, and axially-driven. In this embodiment, the surfaces of the rolls have a plurality of alternating ridges 68 and grooves 70 extending around the circumference of the rolls. In other embodiments, the ridges and grooves may extend parallel to the axes A of the rolls. One or more of such rolls can be used in the various embodiments of the apparatuses described herein.

In the embodiment shown in FIG. 5, and the various other embodiments described herein, the rolls may be meshing, non-meshing, or at least partially intermeshing. The terms "meshing" or "inter-meshing", as used herein, refer to arrangements when the forming elements on one of the components of the forming structure (e.g., roll) extend toward the surface of the other forming structure and the forming elements have portions that extend between and below an imaginary plane drawn though the tips of the forming elements on the surface of the other forming structure. The term "non-meshing", as used herein, refers to arrangements when the forming elements on one of the components of the forming structure (e.g., roll) extend toward the surface of the other forming structure, but do not have portions that extend below an imaginary plane drawn though the tips of the forming elements on the surface of the other forming structure. The term "partially intermeshing", as used herein, refers to arrangements when the forming elements on one of the components of the forming structure (e.g., roll) extend toward the surface of the other forming structure and some of the forming elements on the surface of the first roll have portions that extend between and below an imaginary plane drawn though the tips of the forming elements on the surface of the other forming structure, and some of the elements on the surface of the first roll do not extend below an imaginary plane drawn though the tips of the forming elements on the surface of the other forming structure.

As shown in FIG. 5, the rolls typically rotate in opposite directions (that is, the rolls are counter-rotating). This is also the case for the other embodiments described herein. The rolls may rotate at substantially the same speed, or at different speeds. The phrase "substantially the same speed", as used herein, means that there is less than 0.3% difference in the speed. The speed of the rolls is measured in terms of surface or peripheral speed. Typically, when the web comprises polymeric materials, the rolls will rotate at substantially the same speed. If the web comprises cellulosic materials, the rolls may rotate at different speeds. The rolls may rotate at different surface speeds by rotating the rolls at different axial speeds, or by using rolls that have different diameters that rotate at the same axial speeds. The rolls may rotate at substantially the same speed as the speed at which the web is fed through the nip between the rolls; or, they may rotate at a greater speed than the speed at which the web is fed through the nip between the rolls. In cases where the rolls rotate at different speeds, there can be any suitable difference in surface or peripheral speeds between the rolls such as from greater than or equal to 0.3% up to 100%. One suitable range is between 1-10%. It is generally desirable for the rolls to rotate at speeds which maintain the integrity of the web (that is, not shred the web).

Figure 6:
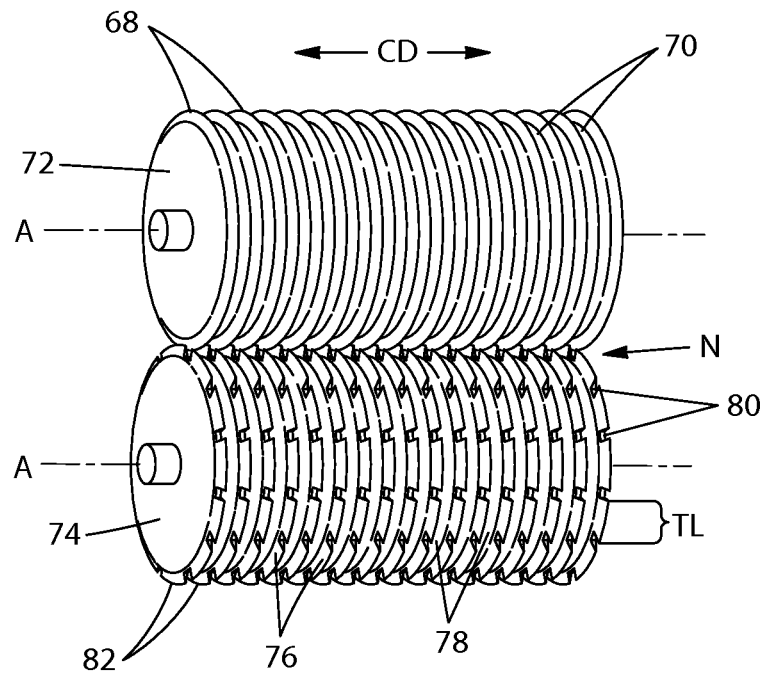
FIG. 6 is an enlarged perspective view of a pair of rolls suitable for use in the methods and apparatuses described herein comprising a ring roll and a SELF roll.

FIG. 6 shows an alternative roll embodiment in which the top roll 72 is a ring roll having circumferential ridges 68 and grooves 70, and the bottom roll 74 is one of The Procter & Gamble Company's "SELF" or "SELFing" rolls. The forming elements on the SELF rolls can be oriented in either the machine direction (MD) or the cross-machine direction (CD). In this embodiment, the SELF roll comprises a plurality of alternating circumferential ridges 76 and grooves 78. The ridges 76 have spaced apart channels 80 formed therein that are oriented parallel to the axis A of the roll. The channels 80 form breaks in the ridges 76 that create discrete forming elements or teeth 82 on the SELF roll 74. In the embodiment shown in FIG. 6, the teeth 82 have their longer dimension oriented in the machine direction (MD). The roll configuration shown in FIG. 6 will be referred to herein as a standard "CD SELF" roll since the teeth are aligned in rows in the MD and CD, and in the usual SELF process, the material being fed into the nip N having such a roll would be stretched in the cross-machine direction (or "CD").

In other embodiments, which are described in the SELF patents that are incorporated by reference herein, the SELF roll can comprise a machine direction, or "MD SELF" roll. Such a roll will have alternating ridges and grooves that are oriented parallel to the axis A of the roll. The ridges in such a roll have spaced apart channels formed therein that are oriented around the circumference of the roll. The channels form breaks in the ridges to form discrete forming elements or teeth on the MD SELF roll. In the case of MD SELF rolls, the teeth have their longer dimension oriented in the cross-machine direction (CD).

Figure 6A:
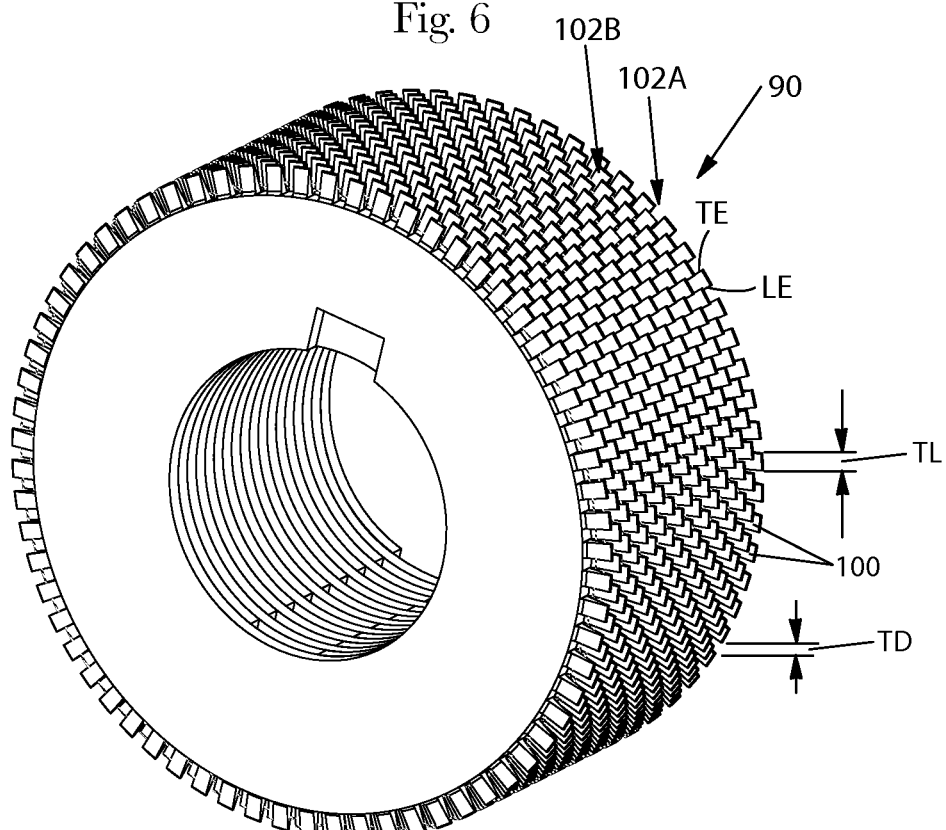
FIG. 6A is an enlarged perspective view of a CD SELF roll with a staggered pattern of teeth thereon.

FIG. 6A is another embodiment of a roll suitable for use in the apparatuses described herein. In this embodiment, the roll 90 comprises a variation of one of The Procter & Gamble Company's CD SELF technology rolls. As shown in FIG. 6A, the surface of the roll has a plurality of spaced apart teeth 100. The teeth 100 are arranged in a staggered pattern. More specifically, the teeth 100 are arranged in a plurality of circumferentially-extending, axially-spaced rows, such as 102A and 102B, around the roll. But for the spacing TD between the teeth in each row, the teeth in each roll would form a plurality of circumferentially-extending, axially-spaced alternating ridges and grooved regions. The tooth length TL and machine direction (MD) spacing TD can be defined such that the teeth in adjacent rows 102A and 102B either overlap or do not appear to overlap when the rolls are viewed from one of their ends. In the embodiment shown, the teeth 100 in adjacent rows are circumferentially offset by a distance of 0.5x (where "x" is equal to the tooth length TL plus the MD spacing TD between teeth in a given row). In other words, the leading edges LE of adjacent teeth in adjacent rows will be offset in the MD by 0.5x. The rolls shown in FIG. 6A can be made in any suitable manner, such as by first cutting the ridges and grooves into the roll, then helically cutting the teeth 100 into the surface of the roll with each helical cut being continuous. If desired, the tooth profile (in particular, the leading and trailing edges) can be modified by using a plunge cut.

The roll 90 can be aligned with an opposing roll which has ridges and grooves therein so that the rows of teeth in one roll align with the grooved regions between the teeth in the opposing roll. The advantage of using CD SELF rolls in the methods described herein is that registration of multiple rolls to provide multiple hits (impacts within multiple nips) is much easier in that it is only necessary to register the toothed regions (that is, to align the toothed regions with the grooved regions on the opposing roll) in the cross-machine direction, and it is not necessary to phase or register the toothed regions in the MD. The staggered tooth pattern allows the web 10 to be mechanically impacted to form features in a staggered pattern.

Figure 6B:
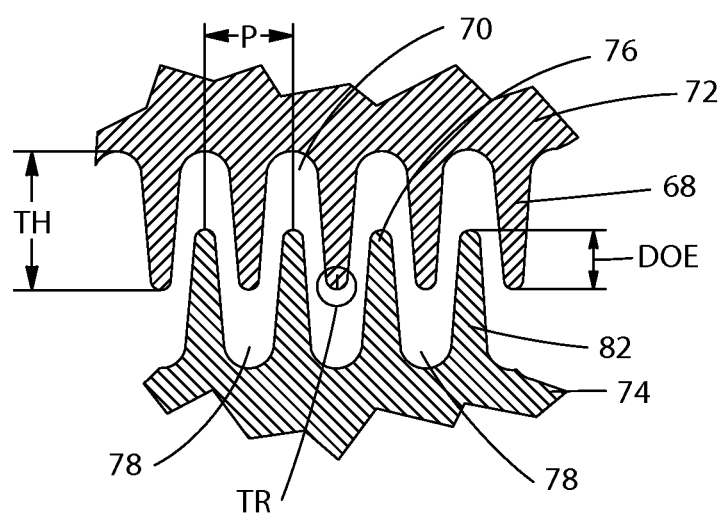
FIG. 6B is a cross-section of a portion of the intermeshing rolls shown in FIG. 6.

FIG. 6B shows in cross section a portion of the intermeshing rolls 72 and 74 shown in FIG. 6 including teeth 82 which appear as ridges 76 and grooves 78 between the teeth 82. The teeth can have a triangular or inverted V-shape when viewed in cross-section. The vertices of teeth are outermost with respect to the surface of the rolls. As shown, teeth 82 that have a tooth height TH, a tooth length TL (FIG. 6), and a tooth-to-tooth spacing (or ridge-to-ridge spacing) referred to as the pitch P. For staggered rolls, the pitch is equal to the spacing between adjacent rows of forming elements. The tooth length TL in such embodiments is a circumferential measurement. The outermost tips of the teeth have sides that are preferably rounded to avoid cuts or tears in the precursor material. The size and shape of the tooth tip may be specified via the tip radius TR. The leading and trailing ends of the teeth may have a radius as well, or the teeth may form a right angle (and have no radius). As shown, the ridges 68 of one roll extend partially into the grooves 78 of the opposed roll to define a "depth of engagement" (DOE) E, which is a measure of the level of intermeshing of rolls 72 and 74. The depth of engagement can be zero, positive for meshing rolls, or negative for non-meshing rolls. The depth of engagement E, tooth height TH, tooth length TL, tooth spacing TD, tip radius TR, and pitch P can be varied as desired depending on the properties of precursor web 10 and the desired characteristics of the formed web 20.

The teeth can have any suitable dimensions. In certain embodiments of the SELF rolls, the teeth 100 can have a length TL ranging from about 0.5 mm (0.020 inches) to about 13 mm (0.512 inches) and a spacing TD from about 0.5 mm to about 13 mm, a tooth height TH ranging from about 0.5 mm to about 17 mm (0.669 inches), a tooth tip radius TR ranging from about 0.05 mm (0.002 inches) to about 0.5 mm (0.020 inches), and a pitch P between about 1 mm (0.040 inches) and 10 mm (0.400 inches). The depth of engagement E can be from about −1 mm to about 16 mm (up to a maximum approaching the tooth height TH). Of course, E, P, TH, TD, TL, and TR can each be varied independently of each other to achieve the desired properties in the web. Another property describing the teeth is their side wall angle. The side wall angle is the angle the longer sides of the teeth make relative to an imaginary vertical line extending outward from the central axis of the roll through the center of the teeth. Any radius at the tips of the teeth is ignored. Typically, the side wall angle of the teeth is defined such that when the rolls are inter-meshing, there is sufficient clearance for the web and the web is not sheared (where portions of the web forced to slip relative to other portions) or pinched by the tooling. However, for some materials, such as those comprising cellulose fibers, it can be advantageous to have smaller clearances and induce shear in the material. Typically, the side wall angle will range from between about 3 to about 15 degrees. The leading and trailing ends of the teeth are typically squared off and have a vertical side wall from the base to the tip of the tooth.

Figure 6C:
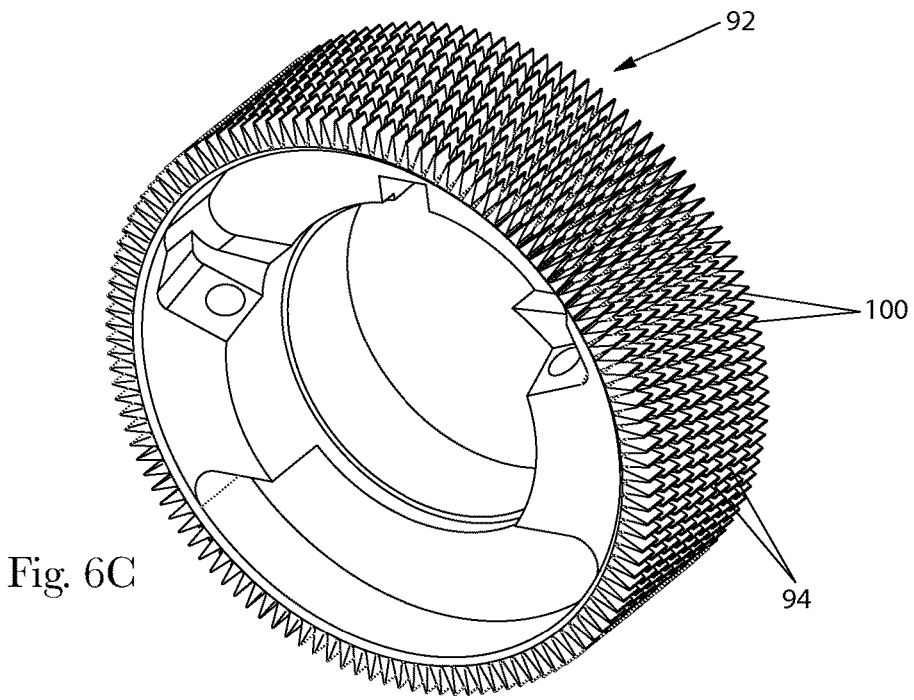
FIG. 6C is an enlarged perspective view of a MD SELF roll with a staggered pattern of teeth thereon.

FIG. 6C shows an alternative roll 92 embodiment which is referred to herein as an "MD staggered SELF" roll in which the teeth 100 are oriented with their longer dimension oriented in the CD and are staggered. The roll 92 has circumferentially extending channels 94 formed between the teeth.

Figure 7:
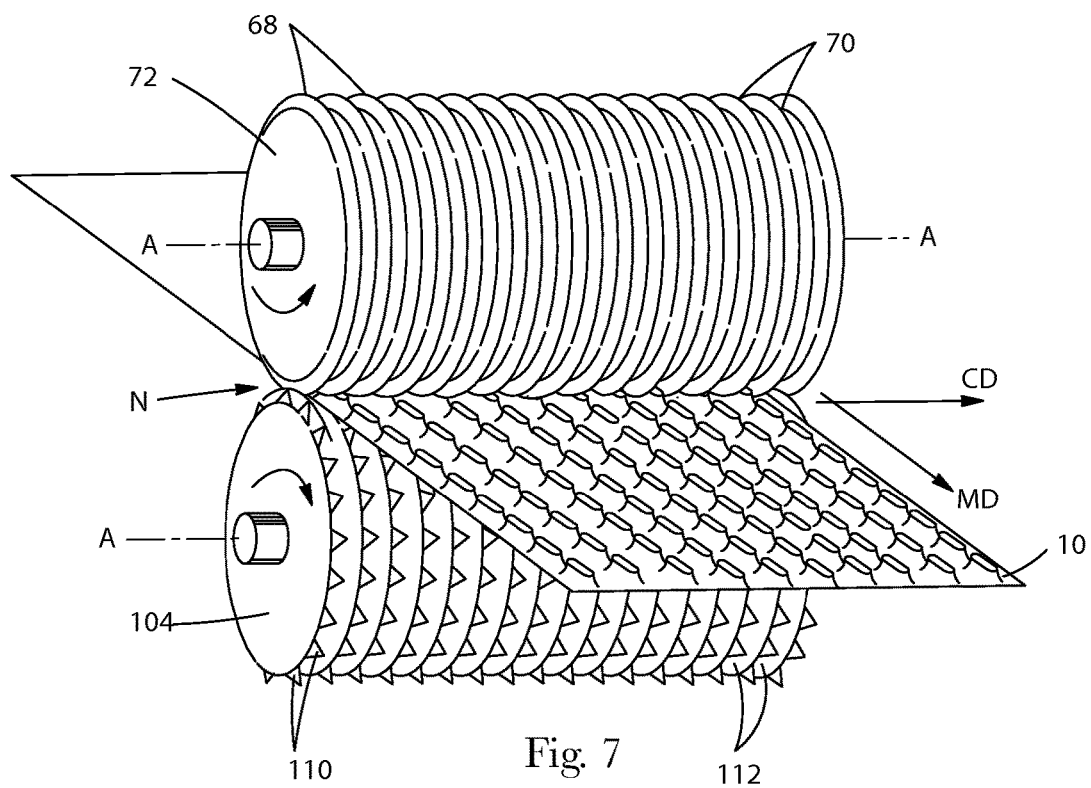
FIG. 7 is an enlarged perspective view of a pair of rolls suitable for use in the methods and apparatuses described herein comprising a ring roll and an RKA roll.
Figure 14:
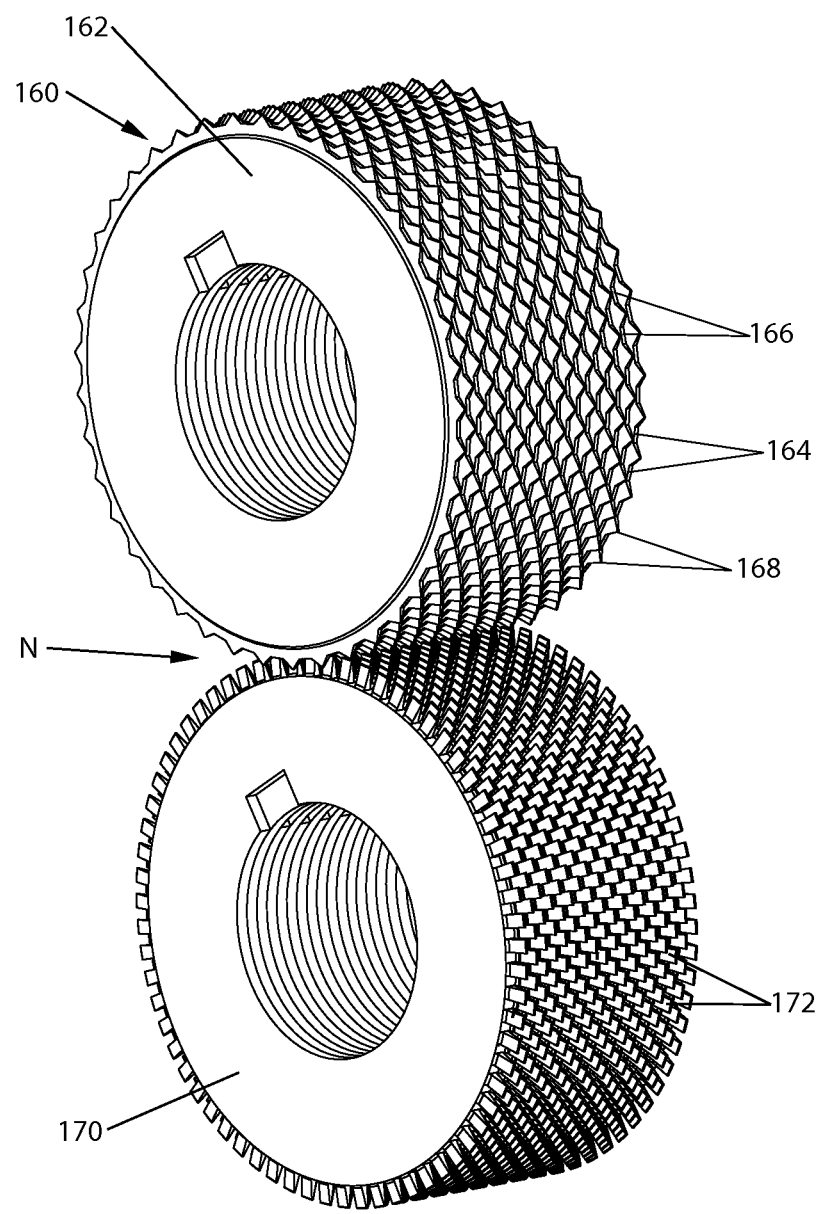
FIG. 14 is an enlarged perspective view of a pair of rolls for use in an apparatus in which one roll is a staggered "raised ridge" rotary knife aperturing (or "RKA") roll and the other roll is a staggered CD SELF roll.
Figure 14A:
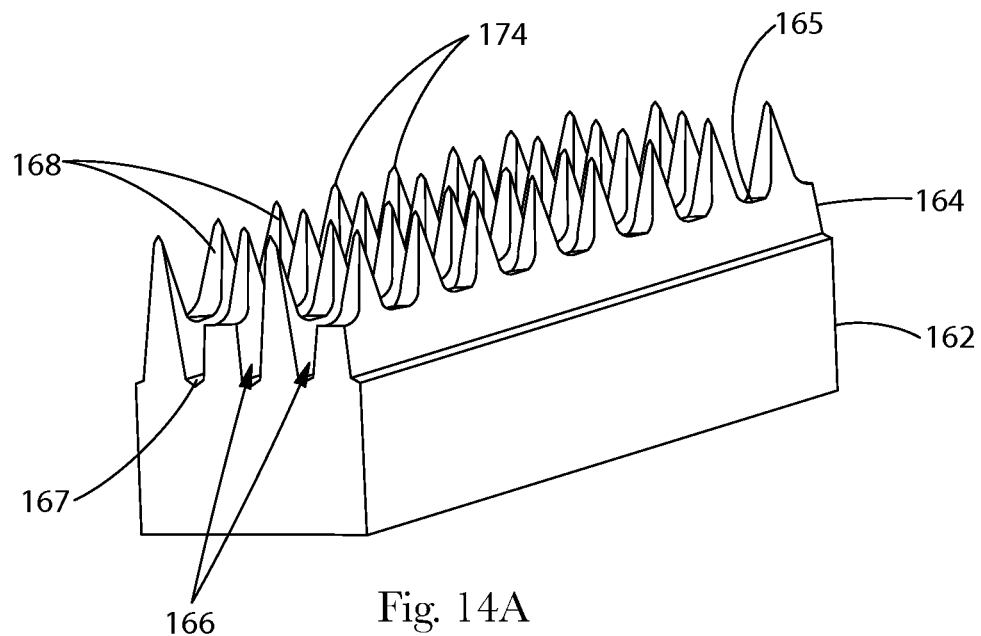
FIG. 14A is an enlarged perspective view of a portion of the surface of the raised ridge RKA roll shown in FIG. 14.
Figure 14B:
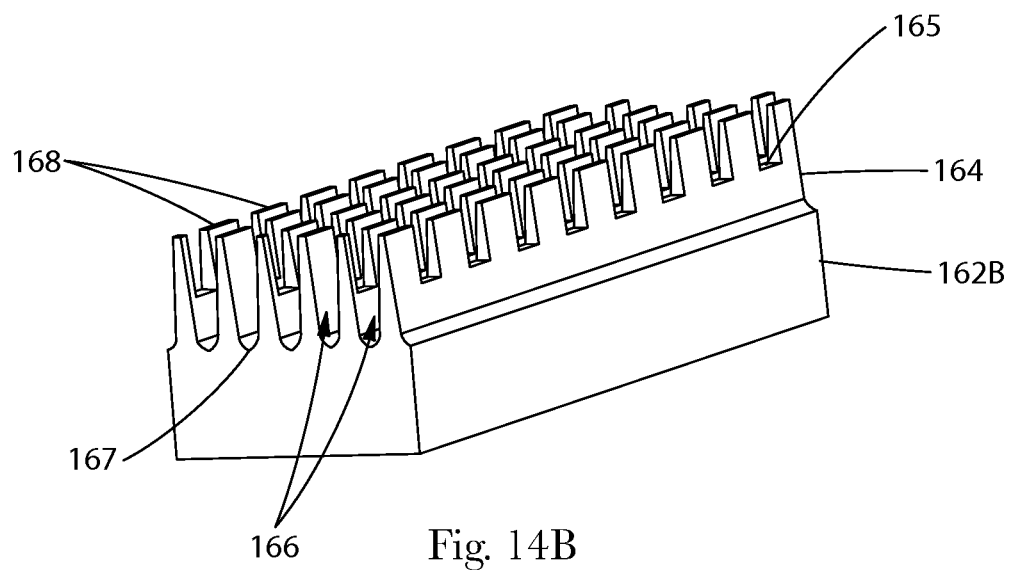
FIG. 14B is an enlarged perspective view of a portion of the surface of a raised ridge SELF roll, which could be used in a process such as that shown in FIG. 14.
Figure 14C:
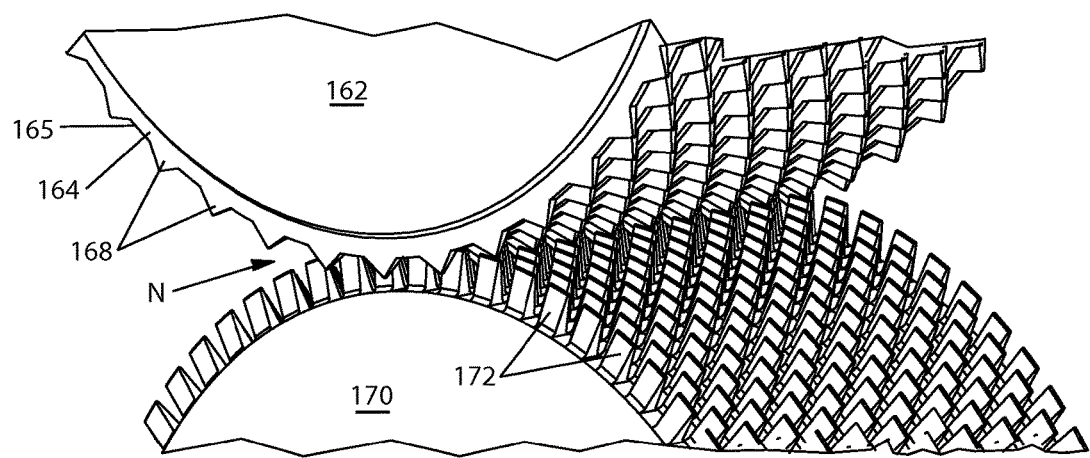
FIG. 14C is an enlarged perspective view of the nip formed between the pair of rolls shown in FIG. 14.

FIG. 7 shows an alternative roll embodiment which the top roll is a ring roll, and the bottom roll is referred to herein as a Rotary Knife Aperturing (or "RKA") roll. As shown in FIG. 7, the rolls comprise a pair of counter-rotating, intermeshing rolls, wherein the top roll 72 comprises circumferentially-extending ridges 68 and grooves 70, and the bottom roll 104 comprises pyramid shaped teeth 110 with at least six sides, the sides being substantially triangular and being tapered from a base to a tip. The teeth 110 are arranged in spaced apart circumferential rows with grooves 112 therebetween. The teeth 110 are joined to the bottom roll 104 at the base, and the base of the tooth has a cross-sectional length dimension greater than a cross-sectional width dimension. Typically, apertures are formed in the web material 10 as the teeth 110 on the RKA roll 104 intermesh with grooves 70 on the other roll 72. With respect to tooth height, tooth spacing, pitch, depth of engagement, and other processing parameters, RKA and the RKA apparatus can be the same as described herein with respect to SELF or micro-SELF. RKA rolls are described in greater detail in U.S. Patent Application Publication No. US 2006/0087053 A1. A variation of such an RKA roll is shown in FIGS. 14 to 14C.

Figure 8:
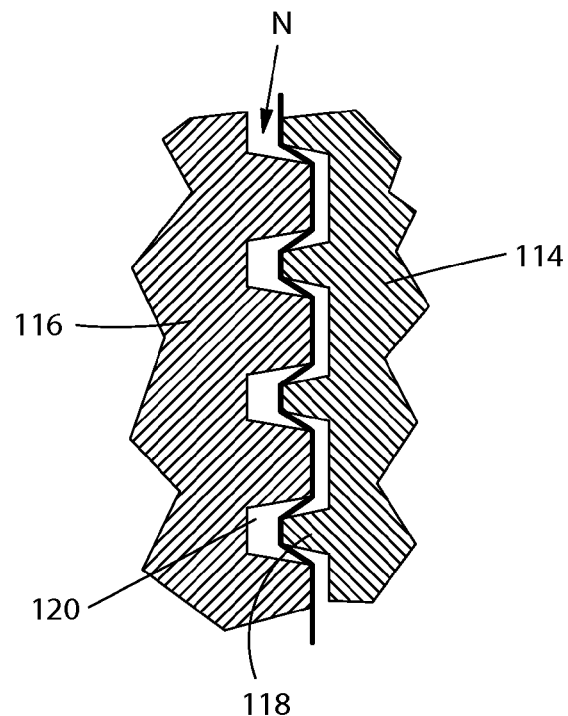
FIG. 8 is a fragmented cross-sectional view through a portion of the nip between a pair of rolls suitable for use in the methods and apparatuses described herein which comprise male/female embossing rolls.

FIG. 8 shows a portion of the nip between a pair of rolls suitable for use in the apparatuses described herein in which the rolls are "male/female embossing" rolls. As shown in FIG. 8, male/female embossing apparatus comprises at least a first and a second patterned roll 114 and 116. The first patterned roll 114 has a male embossing pattern, comprising one or more projections 118 which may be discrete elements (e.g., dot and/or line) embossing elements. The second patterned roll 116 has a female embossing pattern comprising one or more recesses 120, which may be discrete (e.g., dot and/or line configured recesses), into which one or more of the projections of the first patterned roll mesh. The rolls may have matched or unmatched patterns. The elements on the rolls can be of any suitable size and shape. In one non-limiting embodiment detailed in U.S. Pat. No. 6,846,172 B2, Vaughn, the embossing rolls may have unmatched embossing patterns, which were engraved independently from each other. The rolls 114 and 116 in such an embodiment have enlarged sidewall clearances between adjacent, inter-engaged projections 118 and recesses 120 of the embossing patterns. The sidewall clearances can range from about 0.002 inch (about 0.050 mm) to about 0.050 inch (about 1.27 mm). The width of the projections 118 can be greater than about 0.002 inch (about 0.050 mm).

Figure 9:
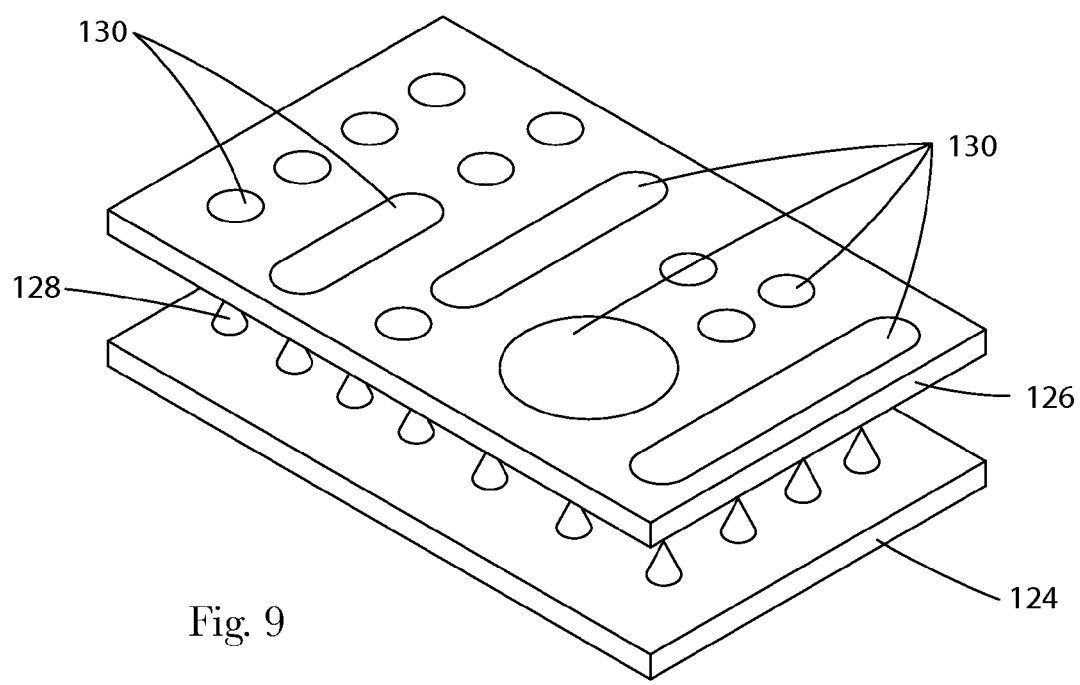
FIG. 9 is an enlarged perspective view of a portion of the surfaces of a pair of rolls suitable for use in the methods and apparatuses described herein.

FIG. 9 shows an alternative non-limiting embodiment in which the surfaces of the rolls 124 and 126 comprise forming elements suitable for forming the micro-textured web in the patent application described above entitled "Process for Making a Micro-Textured Web". The rolls shown in FIG. 9 comprise a roll 124 comprising male forming elements, protrusions or projections 128, and a roll 126 comprising female forming elements, such as discrete and/or continuous voids 130, in the surface of the roll 126. The projections 128 have center-to-center spacings of less than about 800 microns with at least three, at least four, or at least five of its adjacent forming elements. As shown in FIG. 9, the shapes of the female elements 130 may differ from the shapes of the mating male elements 128. FIG. 9 also shows that the female elements 130 can be configured to mate with more than one male element 128.

Figure 9A:
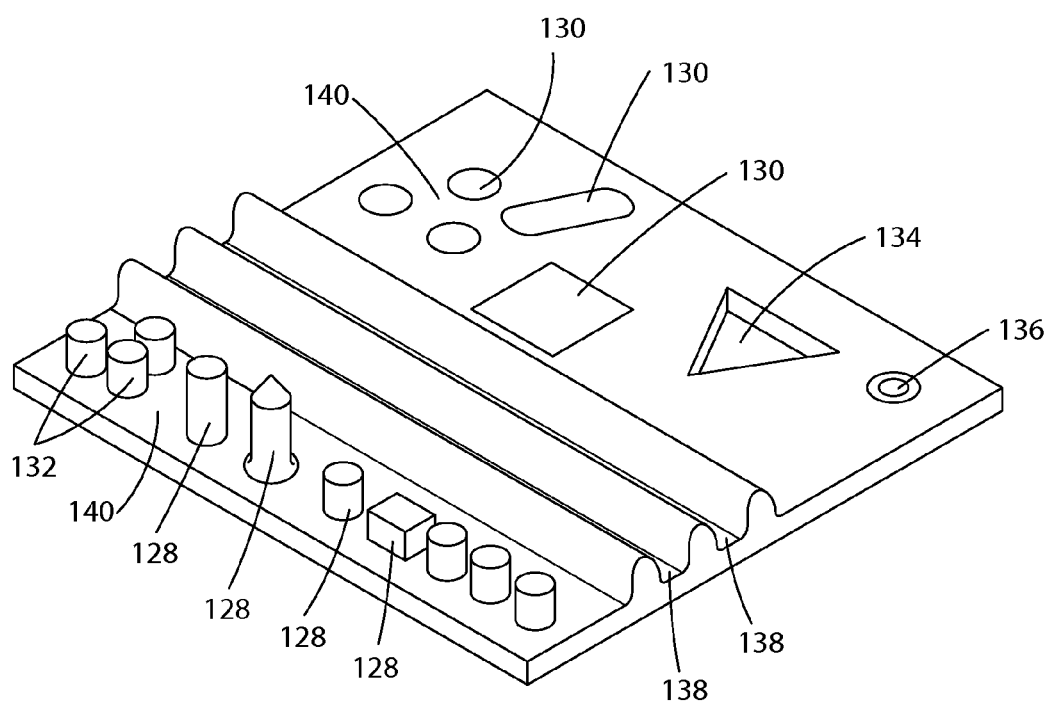
FIG. 9A is a perspective view of a portion of a forming structure having various forming elements.

FIG. 9A shows a portion of a forming structure having a combination of various forming elements. As illustrated in FIG. 9A the forming elements of either or both of the first and second forming structures can include projections such as protrusions 128 or recesses such as voids 130 selected from discrete protrusions 128 (which can take the form of pillars 132), discrete voids 130 (which can take the form of apertures 134 or depressions 136), continuous voids 138, grooves, ridges, or a combination thereof. The forming structures can further include lands 140 completely surrounding the forming elements.

The various types of rolls described above (as well as other types of rolls having forming elements thereon) may be combined in any suitable combinations in the different apparatuses described herein to deform a web of material in a particular manner. The apparatuses may comprise several rolls comprising a single type of roll described above, or any suitable combinations of two or more different types of rolls. The web 10 can be fed through any suitable number of mechanical deformation processes. The number of mechanical deformation nips to which the precursor web is subjected can range from one to between 2 and 100, or more, nips.

Figure 10:
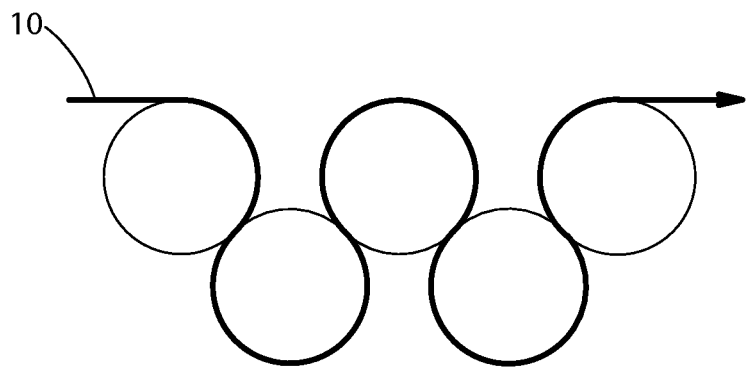
FIG. 10 is a schematic side view of another embodiment of a method and apparatus for deforming a web in which the web wraps at least 180 degrees around one of the rolls.

There can also be variations of the arrangements of rolls in the different apparatuses of interest herein. In the embodiment shown in FIG. 4, the rolls are arranged so that when a web is fed into nips between the rolls, the web 10 will wrap less than 180° around one or more of the rolls. In the variation of this embodiment shown in FIG. 10, the web is fed into the apparatus so that the web 10 will wrap greater than or equal to 180° around one or more of the rolls.

Figure 11:
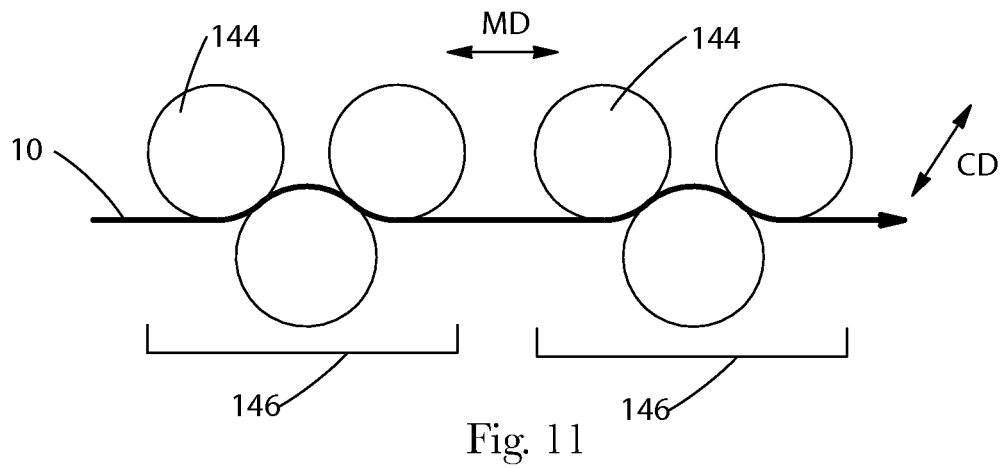
FIG. 11 is a schematic side view of another embodiment of a method and apparatus for deforming a web in which the apparatus comprises a hybrid roll arrangement.

FIG. 11 shows another embodiment of an apparatus that can be used in carrying out the methods described herein. The apparatus shown in FIG. 11 is a hybrid of the nested roll arrangement and the prior art paired roll arrangement. In this embodiment, the apparatus includes rolls 144 arranged in a hybrid arrangement such that there are multiple three to four nested roll clusters 146 that can then be offset relative to each other in the cross-machine direction.

Figure 12:
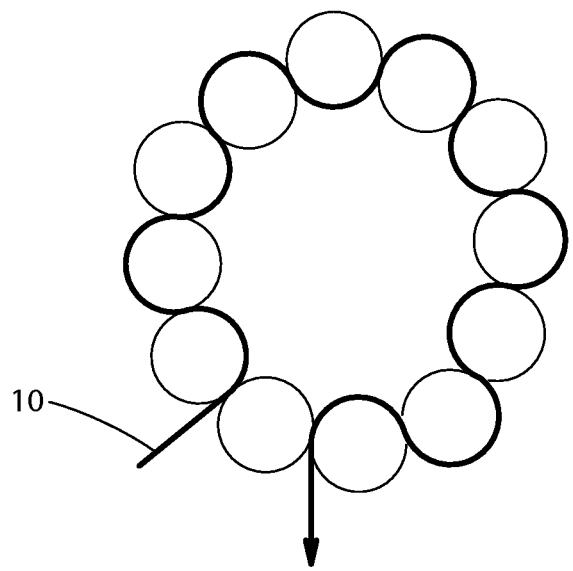
FIG. 12 is a schematic side view of another embodiment of a method and apparatus for deforming a web in which the apparatus comprises a closed loop roll arrangement.

FIG. 12 shows another embodiment of an apparatus that can be used in carrying out the methods described herein. The apparatus shown in FIG. 12 will be referred to as a "nested closed loop" roll arrangement. In this apparatus, there are at least four rolls and the rolls are arranged with their peripheries adjacent to each other in the configuration of a closed loop. The web 10 wraps around the peripheries of the rolls in an alternating configuration with a portion of the web 10 on a portion of a roll that lies inside the periphery of the closed loop, followed by wrapping the web 10 around the next roll about a portion of the roll that lies on the outside of the periphery of the closed loop. In this embodiment, the total number of nips N formed by the rolls is equal to the number of rolls.

Figure 13:
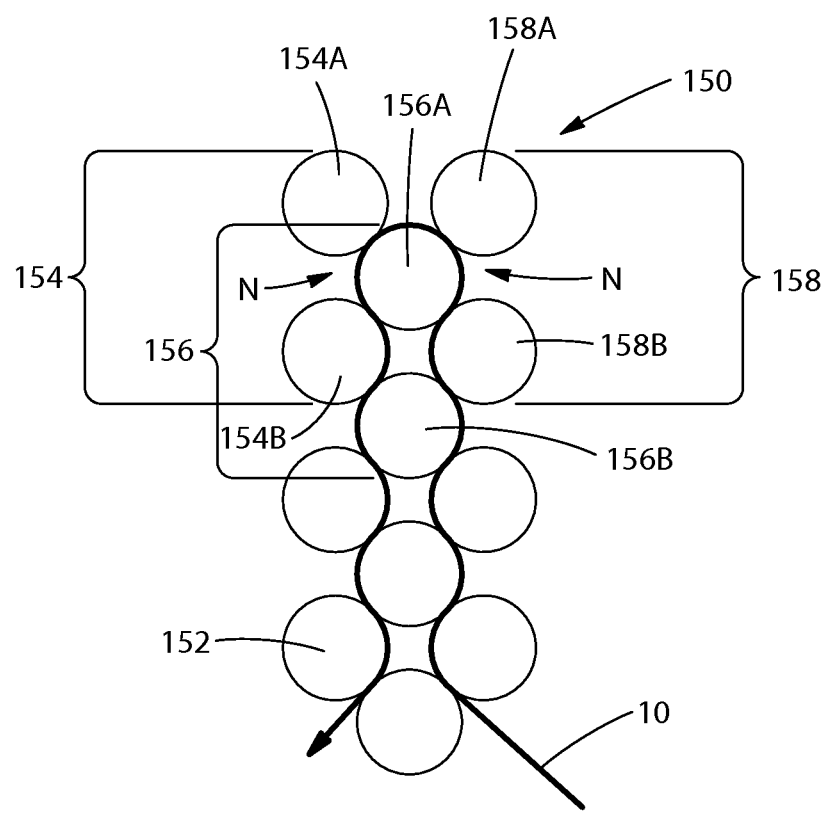
FIG. 13 is a schematic side view of another embodiment of a method and apparatus for deforming a web in which the apparatus comprises a shared bank roll arrangement.

FIG. 13 shows another embodiment of an apparatus 150 that can be used in carrying out the methods described herein. The apparatus 150 shown in FIG. 13 will be referred to as a "nested with shared bank" roll arrangement. In this apparatus, there are at least six rolls designated generally by reference number 152. The rolls are arranged in at least three pairs of rolls comprising a first pair 154 comprising rolls 154A and 154B, a second pair 156 comprising rolls 156A and 156B, and a third pair 158 comprising rolls 158A and 158B. In FIG. 13, additional pairs of rolls are shown. The rolls 156A and 156B in the second pair of rolls form nips N with the rolls in both the first and third pairs of rolls 154 and 158. In this embodiment, some of the rolls form three or more nips (up to four nips). In addition, as can be seen in FIG. 13, in the case of at least one roll such as roll 156B, the web 10 passes adjacent to the roll, leaves the roll, and then returns to contact the roll again. In this embodiment, when there are six rolls, the total number of nips N formed by the rolls is equal to the number of rolls. In variations of this embodiment comprising seven or more rolls, the total number of nips N formed by the rolls can be greater than or equal to the number of rolls. For example, in FIG. 13, there are fourteen nips N formed by only twelve rolls.

III. Methods for Deforming Web Materials and Deformed Web Materials Formed Thereby.

The following figures show non-limiting examples of specific roll arrangements, and the deformed web materials that can be formed thereby.

A. Methods Employing a Roll with Forming Elements Extending from a Raised Ridge

FIG. 14 shows an example of an apparatus 160 that comprises a single pair of rolls that form a single nip N therebetween. The rolls are configured for deforming a web with at least two sets of deformations that are oriented in different directions relative to the surfaces of the web. This can be accomplished by providing one of the rolls 162 with a plurality of ridges 164 and grooves 166 extending around the circumference of the roll and a plurality of first spaced apart forming elements 168 extending outwardly from the top surface of the ridges 164, and providing a second roll 170 with a plurality of second forming elements 172 on its surface in which the tips of the second forming elements extend inward toward the axis of the first roll to a depth beyond the top of at least some of the ridges 164 on the first roll 162.

The top roll 162 in the apparatus shown in FIG. 14 can comprise any suitable type of roll that meets the criteria set out above. In the embodiment shown in FIG. 14, the top roll 162 is a variation of the RKA roll shown in FIG. 7. This particular variation will be referred to herein as a "raised ridge RKA roll". As shown in FIG. 14, the top roll 162 has a plurality of ridges 164 and grooves 166 extending around the circumference of the roll on the surface of the roll. As shown in FIG. 14A, the ridges 164 have a top surface 165 and the grooves 166 have a bottom surface 167. The ridge height is defined as the distance between the top surface of the ridge 165 and the bottom surface 167 of the grooves 166. The tooth height is defined as the distance between the tip 174 of the forming element 168 and the bottom surface 167 of the grooves 166. In this embodiment, the distance between the top surfaces 165 of the ridges 164 and the bottom surfaces 167 of the grooves 166 is substantially the same around the circumference of the roll. The ridge height depends on the amount of deformation that is required to form the second set of features. The ridge height is typically at least about 25% up to less than about 95% of the tooth height. The roll 162 further comprises a plurality of spaced apart first forming elements in the form of teeth 168 extending outwardly from the top surface of the ridges 164, as shown in greater detail in FIGS. 14A and 14C. The teeth 168 taper from the base where they are joined to the top surface 165 of the ridges 164 to a pointed tip. As shown in FIG. 14A, the configuration of the roll 162 is such that the top surface 165 of the ridges 164 are disposed between the tips 174 of the teeth 168 and the bottom surface 167 of the grooves 166, directionally relative to the axis A of the roll.

The bottom roll 170 in the apparatus shown in FIG. 14 can comprise any suitable type of roll that meets the criteria set out above. The bottom or second roll 170 in FIG. 14 should, thus, comprise a roll with discrete second forming elements 172 thereon in which the tips of these second forming elements 172 extend inward toward the axis of the first roll 162 to a depth beyond the top 165 of at least some of the ridges 164 on the first roll, top roll 162. The bottom roll 170 can, for example, comprise a standard CD SELF roll (as in FIG. 6), a staggered CD SELF roll (as in FIG. 6A), an RKA roll (as in FIG. 7), another raised ridge RKA roll, or a raised ridge SELF roll (as in FIG. 14B). In the particular embodiment shown in FIG. 14, the bottom roll 170 comprises a staggered CD SELF roll such as the roll shown in FIG. 6A. Of course, the positions of the rolls shown in FIG. 14 can be reversed, or be arranged in any other suitable orientation (such as side-by-side) so long as they form a nip therebetween.

The web 10, in its initial state, can be thought of as being comprised entirely of undeformed regions. When the web 10 is fed into the nip N between the rolls shown in FIG. 14, the web is deformed: (i) by the first forming elements 168 of the top roll 162 to form a plurality of spaced apart first features in first locations; and (ii) by the second forming elements 172 of the bottom roll 170 in different locations than the first locations to form a plurality of spaced apart second features in second locations such that the second features are distributed between the first features. As the first set of features is formed, the raised ridge supports the web so that the second set of features can be formed in the opposite direction. If the raised ridge is not present, the set of features that is easiest to form (such as apertures in this example) will be formed first, and the second set of features will never be formed, or if the second features are formed, they will not be formed in the desired feature size and/or shape.

Figure 15:
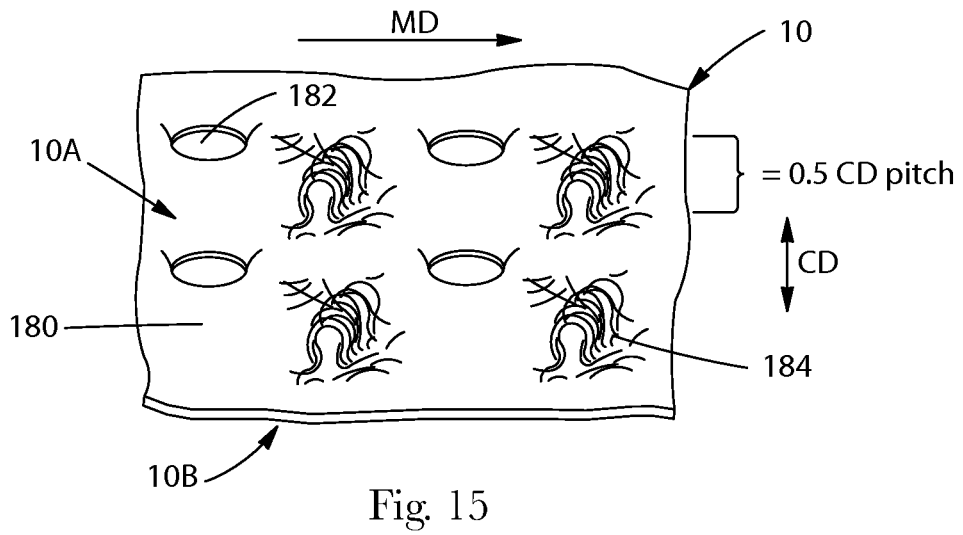
FIG. 15 is a top perspective view of one example of a web that can be formed by using a variation of the rolls in FIG. 14.

FIG. 15 shows an example of a web 10 that can be made by a variation of the apparatus shown in FIG. 14. The variation of the apparatus used to form the web shown in FIG. 15 comprises an RKA roll for the upper roll 162 as shown in FIG. 14, but with a standard (non-staggered tooth) pattern, and the lower roll 170 is replaced with a standard (non-staggered) CD SELF roll such as shown in roll 74 in FIG. 6. As used herein, the term "standard" means that the forming elements on a single roll are aligned in rows in the machine direction and the cross-machine direction. The rolls 162 and 170 are aligned or phased in the machine direction such that the forming elements 172 on the SELF roll align with the ridges 164 on the RKA roll. As the teeth 168 on the RKA roll 162 penetrate the web 10, the ridges 164 between the teeth 168 on the RKA roll support the web 10 such that the SELF teeth 172 can penetrate the web 10 and simultaneously form elements in the opposite direction.

In the example of the web shown in FIG. 15, the web has a first surface 10A and a second surface 10B and discrete deformations formed therein. The web 10 comprises: substantially undeformed regions 180, which correspond to the first and second surfaces 10A and 10B of the web. In FIG. 15, web 10 further comprises a plurality of spaced apart first features such as apertures 182, and a plurality of spaced apart second features such as tufts 184. The apertures 182 are pushed out of the plane of the web 10 in one direction (downward as viewed in FIG. 15), and the tufts 184 are pushed out of the plane of the web 10 in the opposite direction. As shown in FIG. 15, the apertures 182 are aligned in rows in the MD and the CD. The tufts 184 are also aligned in rows in the MD and CD. The rows of tufts 184 are, however, aligned between the rows of apertures 182 in the MD and the CD, with the rows of tufts 184 being offset in the CD such that they are separated from the adjacent rows of apertures 182 by a distance of up to one half of the pitch between the apertures 182 in the cross-machine direction (CD).

FIG. 15 shows one example of a combination of features that can comprise the first and second formed features. Although combinations of apertures and tufts are frequently shown in the drawings, it should be understood, however, that in all of the embodiments described herein the first features and second features are not limited to apertures and tufts, and that the first features and second features can, depending on the configuration of the forming elements, comprise any other suitable combinations and configurations of features. The present invention is, thus, not limited to the combination of features shown in FIG. 15 and the figures that follow, and is intended to cover all possible combinations and configurations of the features described herein. In addition, the present invention is not limited to forming two features in a web in first and second locations. It is also contemplated that additional features can be formed into the web in third, fourth, fifth, or more, locations.

The configuration of the rolls shown in FIG. 14 may provide a number of advantages. The rolls can, within a single nip, form a web that has intermixed features oriented in multiple directions (for example, apertures 182 may be pushed out of the plane of the web in one direction, and tufts 184 may be pushed out of the plane of the web in the opposite direction). The features may be distributed within the web so that they are consistently less than one pitch apart. Thus, if two different types of features are formed, the spacing between dissimilar elements may be less than spacing between like elements.

Figure 14D:
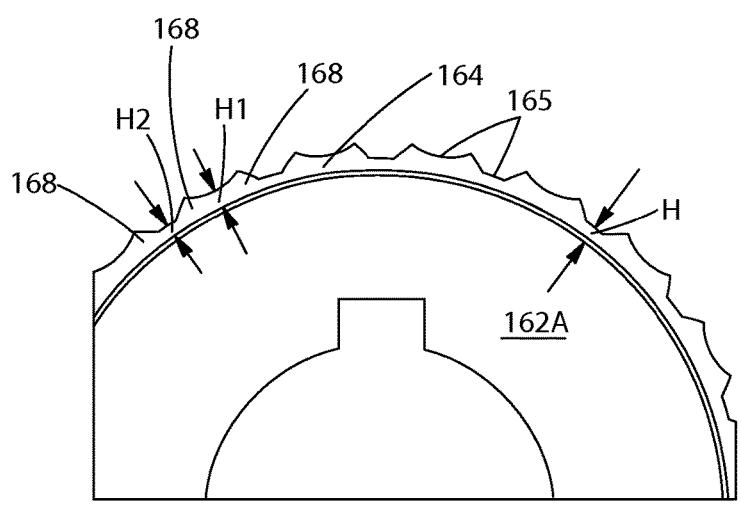
FIG. 14D is an enlarged side view of a portion of the surface of an alternative raised ridge RKA roll shown in FIG. 14.

Various alternative embodiments of the raised ridge rolls are possible. For example, FIG. 14D shows an alternative embodiment of the raised ridge RKA roll 162A in which the height, H, of the ridges 164 varies between at least some of the teeth 168. In such a case, the top surface 165 of at least one ridge 164 between a pair of forming elements 168 will have a height H1 that is at least 20% greater than the height H2 of another ridge 164 between another pair of forming elements 168. This roll 162A could be used in a process such as that shown in FIG. 14 in place of the raised ridge RKA roll 162. FIG. 14B shows yet another alternative type of roll that could be used, which will be referred to herein as a "raised ridge SELF roll" 162B. As shown in FIG. 14B, this roll 162B has teeth 168 that are configured to form ridges rather than points.

A variation of the apparatus shown in FIG. 14 can utilize an additional roll and a two step process. The apparatus used for such a variation can resemble the planetary roll arrangement shown in FIG. 2. This apparatus need only comprise a central roll 32 and a first satellite roll 34 and a second satellite roll 36. The apparatus differs from known planetary roll arrangements in that it utilizes the new roll configurations described herein. The objective of such a modified planetary roll arrangement is to form two sets of deformations in the web, and to further deform one of the sets of deformations at one of the nips. In such an apparatus, the central roll 32 can comprise a raised ridge roll, such as a raised ridge SELF roll in FIG. 14B or a raised ridge RKA roll, such as rolls 162 or 162A. One of the satellite rolls 34 or 36 comprises a roll having a plurality of discontinuous ridges and grooves thereon in the form of discrete forming elements. The other satellite roll has continuous ridges and grooves thereon, such as a ring roll. The nip between the raised ridge central roll 32 and the satellite roll having discrete forming elements will be referred to herein as the "primary nip" since this is the nip where two sets of deformations are formed. The nip between the raised ridge central roll 32 and the satellite roll that has continuous ridges and grooves thereon will be referred to herein as the "secondary nip". The secondary nip can occur either before or after the primary nip. The depth of engagement can be the same in the primary and secondary nips; or, the depth of engagement may vary between nips (for example, so that the depth of engagement at the downstream nip is greater).

In one non-limiting example of a case in which the secondary nip occurs before the primary nip, the first satellite roll 34 can comprise a ring roll and the second satellite roll 36 can comprise a SELF roll. In such an embodiment, at the secondary nip between the raised ridge central roll 32 and the ring roll 34, the raised ridge central roll 32 will form a first set of deformations into the web (for example, three dimensional apertures if the central roll 32 is a raised ridge RKA roll, or protrusions if the central roll 32 is a raised ridge SELF roll). In addition, the ring roll in the secondary nip can pre-strain the web in the same CD location that the SELF roll will impact the web downstream in the primary nip, pre-weakening the web and making it easier to form the second set of deformations. Then, downstream at the primary nip between the raised ridge central roll 32 and the second satellite SELF roll 36, a second set of deformations can be formed into the web by the SELF roll and the first set of deformations can be enlarged by the raised ridge central roll 32.

In one non-limiting example of a case in which the secondary nip occurs after the primary nip, the first satellite roll 34 can comprise a SELF roll and the second satellite roll 36 can comprise a ring roll. In such an embodiment, at the primary nip between the raised ridge central roll 32 and the first satellite SELF roll 34, these rolls will combine to form a first and a second set of deformations into the web (for example, the central roll 32 will form three dimensional apertures if the central roll 32 is a raised ridge RKA roll, or protrusions if the central roll 32 is a raised ridge SELF roll, and the SELF roll will form protrusions or tufts). Then, downstream at the secondary nip between the raised ridge central roll 32 and the second satellite ring roll 36, the first set of deformations formed by the raised ridge central roll 32 can be enlarged by the raised ridge central roll 32.

The variation of the apparatus of FIG. 14 described above may be useful in providing greater flexibility in forming deformations than the apparatus shown in FIG. 14. In the apparatus shown in FIG. 14, which has a single nip, the amount of deformation that can be imparted by the first and second forming components 162 and 170 is dependent upon the geometry of the tooling and the depth of engagement of the forming components. These aspects are tied to one another when there is a single nip. The variation of the apparatus described above may provide the advantages of: (1) allowing independent control over formation of the first and second sets of deformations that are being formed; and, in some configurations, (2) pre-straining the material in the locations where the second set of deformations are to be formed.

B. Methods Utilizing Multiple Deformation Steps

The methods of interest herein may also utilize multiple deformation steps. Such multiple deformation steps can be carried out by any suitable apparatuses described in the foregoing section of this description. Although the methods that utilize multiple deformation steps are shown as being carried out on nested apparatuses having a relatively small number of rolls in a standard nested arrangement, it should be understood that this is done for simplicity of illustration, and any of the apparatuses described herein (such as the hybrid, closed loop, and shared bank apparatuses) could be used with any suitable number of rolls in order to carry out the desired deformation.

Apparatuses that utilize multiple deformation steps for forming inter-mixed features typically comprise a minimum of three nips formed by a minimum of four rolls. Two of the nips are deformation nips in which the web is permanently deformed to form a first-time deformed precursor web with a first set of features and a second-time deformed precursor web with a second set of features. The third nip may be a transfer nip disposed between the deformation nips in which the web is not permanently deformed. The transfer nip may be used to dispose a different side of the web for a subsequent deformation step such that different sets of features can be formed on opposite sides of the web. The transfer nip can also be used to off-set the rolls in subsequent deformation steps such that the different sets of features can be formed in different CD lanes, enabling tighter spacing of features. Depending on the configuration and arrangement of the rolls, the forming elements in the second deformation nip can contact the web in one of the following locations: 1) the same location as in the first deformation nip; 2) at least partially different locations wherein at least some of the locations at least partially coincide with the first location; and 3) in completely different locations.

The deformation nips comprise a first roll with discrete male elements thereon and a second roll that is capable of mating with the first roll to form discrete features. The first roll may comprise a SELF roll, RKA roll, or male embossing roll. The second roll preferably comprises a ring roll or a female emboss roll, depending on the type of roll that is chosen for the first roll. In some the cases, it may be desirable for the second roll to comprise discrete male elements, for example when it is desired to use the process to reduce the density of drylap or other wetlaid structures. The rolls that comprise the transfer nips may be capable of being arranged in either: i) a tip-tip configuration in which the outwardmost portions on the surface of the rolls substantially align to form a nip, or ii) an off-set configuration in which the outwardmost portions on the surface of the rolls are capable of meshing. Any of the rolls listed above (SELF roll, RKA roll, ring roll, male embossing roll, female embossing roll) can be used for the rolls in the transfer nip. Several specific embodiments are detailed below in which the rolls with the discrete male forming elements thereon that are used to form deformations into the web are the first and the last rolls in the apparatus.

Figure 16:
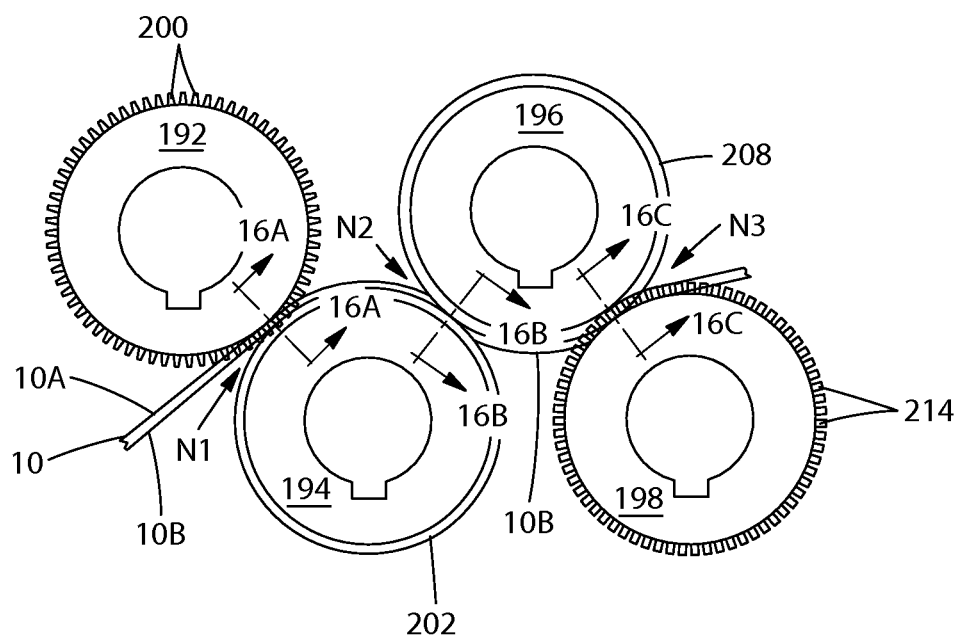
FIG. 16 is a schematic side view of another embodiment of a method and apparatus for deforming a web.

FIG. 16 shows an example of an apparatus 190 for deforming a web 10 that comprises multiple rolls arranged in a nested configuration. In this embodiment, the apparatus has four rolls 192, 194, 196, and 198. In apparatuses that utilize multiple deformation steps, some of the nips can be used to deform the web, and some of the nips, particularly the intermediate nips located between the nips used to deform the web, can be used for other purposes, such as transferring the web. For example, in some non-limiting embodiments, such as shown in FIG. 16, some of the rolls 194 and 196 can form an intermediate nip N2 which is used to expose a different side of the web for a subsequent deformation step. It should be understood, however, that in any of the embodiments described herein, the rolls with the discrete male forming elements thereon that are used to form deformations into the web need not be the first and the last rolls in the apparatus. In other embodiments, the rolls with the discrete male forming elements thereon can comprise one or more of the intermediate rolls. For example, the rolls with the discrete male forming elements thereon can comprise the two intermediate rolls forming the transfer nip, and the first and last rolls can comprise rolls with mating female forming elements. Alternatively, the rolls may alternate such that every other roll contains discrete male forming elements thereon and every other roll in between comprises rolls with mating female forming elements thereon. Regardless of the configurations of the rolls, there may be at least one non-permanently deforming transfer step in-between the deformation steps.

Figure 16A:
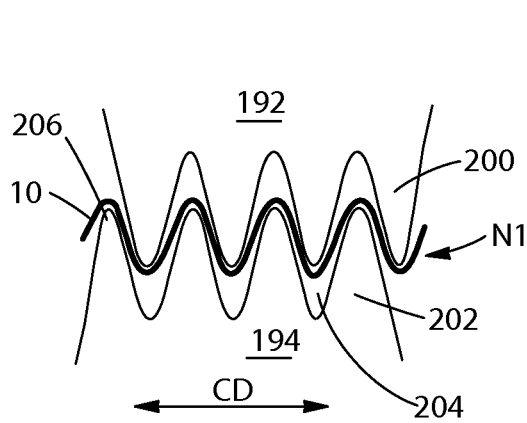
FIG. 16A is an enlarged partially fragmented cross-sectional view of the teeth of the first and second rolls of the apparatus shown in FIG. 16 taken along lines 16A-16A.

The process carried out in the example on the apparatus shown in FIG. 16 comprises initially feeding the web 10 into a first nip N1 that is formed between a first pair of generally cylindrical intermeshing rolls comprising a first roll 192 and a second roll 194. In this example, the first roll 192 has a surface with discrete male forming elements 200 thereon. The first roll 192 can comprise any suitable type of roll having such properties including, but not limited to: a male embossing roll, an RKA roll, or a SELF roll. In the embodiment shown in FIG. 16, the first roll 192 comprises an RKA roll. The second roll 194 should be capable of forming a nip with the first roll 192 to form permanent deformations in the web 10. The second roll 194 should also be capable of cooperating with the third roll 196 to maintain control of the web 10 and transfer the web, without permanently deforming the same, to a downstream deforming nip. The second roll 194 has a surface with projections 202 and/or recesses 204 thereon, wherein any projections 202 or the portions of the roll between any recesses form the radially outwardmost portions 206 on the surface of the second roll 194. The second roll 194 can comprise any suitable type of roll having such properties including, but not limited to: a male or female embossing roll, a ring roll, or a SELF roll. In the embodiment shown in FIG. 16, the second roll 194 comprises a ring roll. The nip N1 between the intermeshing first and second rolls 192 and 194 is shown in cross-section in FIG. 16A.

The third roll 196 should also be capable of cooperating with the second roll 194 to maintain control of the web 10 and transfer the web, without permanently deforming the same, to a downstream deforming nip. The third roll 196 has a surface with projections 208 and/or recesses 210 thereon, wherein any projections 208 or the portions of the roll between any recesses 210 form the radially outwardmost portions 212 on the surface of the third roll 196. The third roll 196 can comprise any suitable type of roll having such properties including, but not limited to: a male or female embossing roll, a ring roll, or a SELF roll. In the embodiment shown in FIG. 16, the third roll 196 comprises a ring roll. The nip N2 between the second 194 and third 196 rolls is shown in cross-section in FIG. 16B. As shown in cross-section in FIG. 16B, the third roll 196 does not intermesh with the second roll 194. Instead, the rolls are arranged so that the outwardmost portions 202 on the second roll 194 align with the outwardmost portions 212 of the third roll 196. The alignment of rolls with the web shown in FIG. 16B may be referred to herein as a "tip-to-tip" transfer. This transfers the web 10 and orients the web so that the second surface 10B of the web 10 faces outward on the third roll 196. For rolls comprising ridges and grooves, the tip-tip transfer also aligns the rolls in the subsequent deformation nip such that the second set of formed features are substantially aligned in the CD with the first set of formed features. The gap between the transfer rolls is set such that the web is not permanently deformed in the nip, but the rolls are in close enough proximity to ensure there are no free spans of web greater than 2 cm and the web remains in registration.

The web 10 is then fed into a third nip N3 between the third roll 196 and a fourth roll 198. The nip N3 between the intermeshing third and fourth rolls is shown in cross-section in FIG. 16C. The fourth roll 198 has a surface with discrete forming elements 214 thereon. The fourth roll 198 can comprise any suitable type of roll having such properties including, but not limited to: a male embossing roll, an RKA roll, or a SELF roll. In the embodiment shown in FIG. 16, the fourth roll 198 comprises a SELF roll. If it is desired to create intermixed features as shown in FIGS. 17 and 18, the rolls in the deformation nips should be phased such that the first and second sets of formed features are formed in at least partially different locations relative to each other.

The elements on the various rolls shown in FIG. 16 include, but are not limited to: cross-machine direction elements, machine direction elements, elements that are aligned in rows or have a staggered alignment of forming elements, elements that are not aligned in rows with uneven/irregular spacing, and elements on rolls having a raised ridge configuration. The meshing pairs of rolls should be designed and configured in a way that allows for sufficient clearance of the web at the desired depth of engagement.

When the precursor web 10 is fed into the first nip N1 in the apparatus shown in FIG. 16, the web 10 is deformed in a first location to form a first set of formed features in the web 10. The first set of formed features comprises portions in first locations of the web that extend outward from the second surface 10B of the web. Examples of such formed features are shown in FIGS. 17 and 18, which are described in greater detail below. The type and alignment of the formed features depends on the configuration and alignment of the rolls. The precursor web 10 is then fed into a second nip N2 to contact the web 10 and transfer the web from the second roll 194 to the third roll 196. This transfers the web 10 and orients the web so that the second surface 10B of the web 10 faces outward on the third roll 196. When the web is fed into the third nip N3 between the third and fourth rolls 196 and 198, the web 10 is deformed in second locations in which at least some of the forming elements 214 in the third nip N3 deform the first-time deformed precursor web at least partially in different locations and in a different orientation than the precursor web was deformed in the first nip N1. In the third nip, the web 10 is permanently deformed in second locations to form a second set of formed features in the web. The second set of formed features comprises portions that extend outward from the first surface 10A of the web to form a second time-deformed precursor web.

Figure 17:
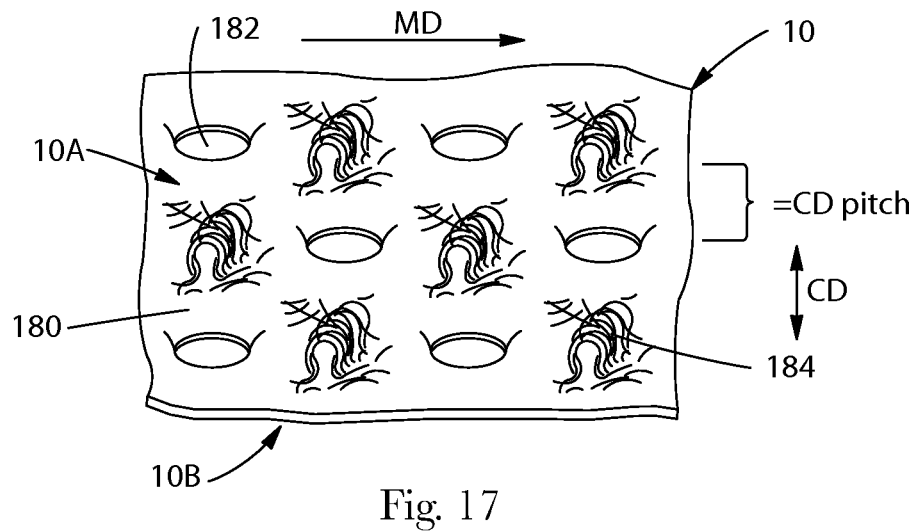
FIG. 17 is a top perspective view of one example of a web that can be formed by using the rolls in FIG. 16 in which the first and last rolls have a staggered pattern of forming elements thereon.
Figure 18:
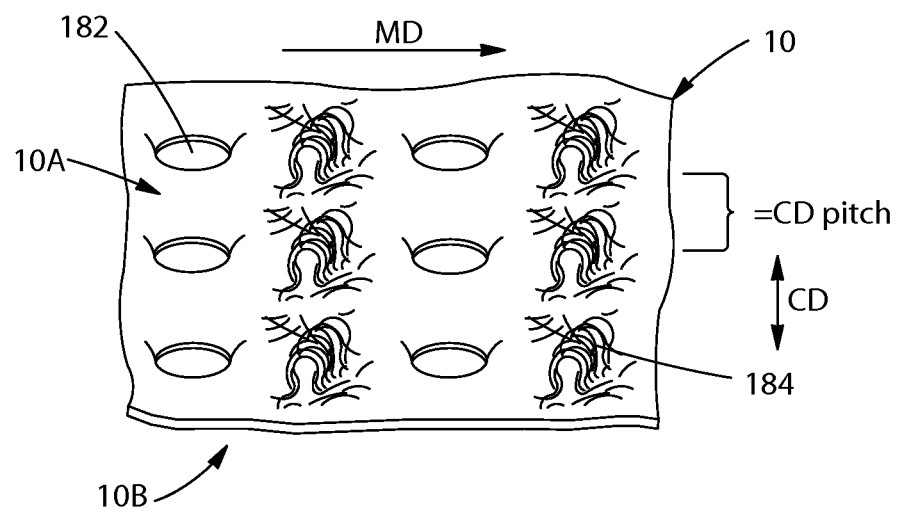
FIG. 18 is a top perspective view of one example of a web that can be formed by using the rolls in FIG. 16 in which the first and last rolls have a standard (or linear) pattern of forming elements thereon.

FIG. 17 shows an embodiment of a nonwoven web 10 made using the apparatus shown in FIG. 16, in which the first roll 192 is a staggered RKA roll and the fourth roll 198 is a staggered CD SELF roll. In FIG. 17, the first features (in the first locations), which are formed in the first nip N1, comprise a plurality of spaced apart apertures 182. The second features (in the second locations), which are subsequently formed in the third nip N3, comprise a plurality of spaced apart tufts 184. The apertures 182 are pushed out of the plane of the web in one direction (downward as viewed in FIG. 17), and the tufts 184 are pushed out of the plane of the web in the opposite direction (upward). As shown in FIG. 17, the apertures 182 are aligned in rows in the MD, the CD, and diagonally. The tufts 184 are also aligned in rows in the MD, the CD, and diagonally. However, there are spaces between each of the apertures 182 and a tuft 184 is located in each of these spaces. In other words, the tufts 184 are intermixed with the apertures. The first and second features may lie in substantially the same MD and CD rows so that the first and second features alternate in the MD and CD. In this embodiment, the tufts 184 may be separated from the adjacent rows of apertures 182 by a distance in the cross-machine direction (CD) approximately equal to the pitch between the rows of apertures 184.

When the features are described as being substantially aligned, or lying in substantially the same rows, this refers to at least a majority of the specified features. Thus, if the second features are described as lying substantially in the same rows as the first features, at least a majority of the second features lie in the same rows as the first features. Of course, in any of the embodiments described herein, the first and second features may be offset relative to each other so that they do not lie in substantially the same rows. The second features also need not be spaced between the first features such that there in equal spacing between the features on each side.

FIG. 18 shows an embodiment of a nonwoven web 10 made using the apparatus shown in FIG. 16, in which the first roll 192 is a standard RKA roll and the fourth roll 198 is a standard CD SELF roll. In FIG. 18, the first features, which are formed in the first nip N1, comprise a plurality of spaced apart apertures 182, and the second features, which are subsequently formed in the third nip N3, comprise a plurality of spaced apart tufts 184. The apertures 182 are pushed out of the plane of the web 10 in one direction (downward as viewed in FIG. 18), and the tufts 184 are pushed out of the plane of the web 10 in the opposite direction (upward). As shown in FIG. 18, the apertures 182 are substantially aligned in rows in the MD and the CD. The tufts 184 are also substantially aligned in rows in the MD and CD. The rows of tufts 184 are, however, aligned between the rows of apertures 182 in the MD so that there is a row of tufts 184 between every row of apertures 182, and the tufts 184 and apertures 182 alternate in each MD row.

The distance between the features in adjacent MD rows is approximately equal to the pitch in the cross-machine direction (CD).

Figure 19:
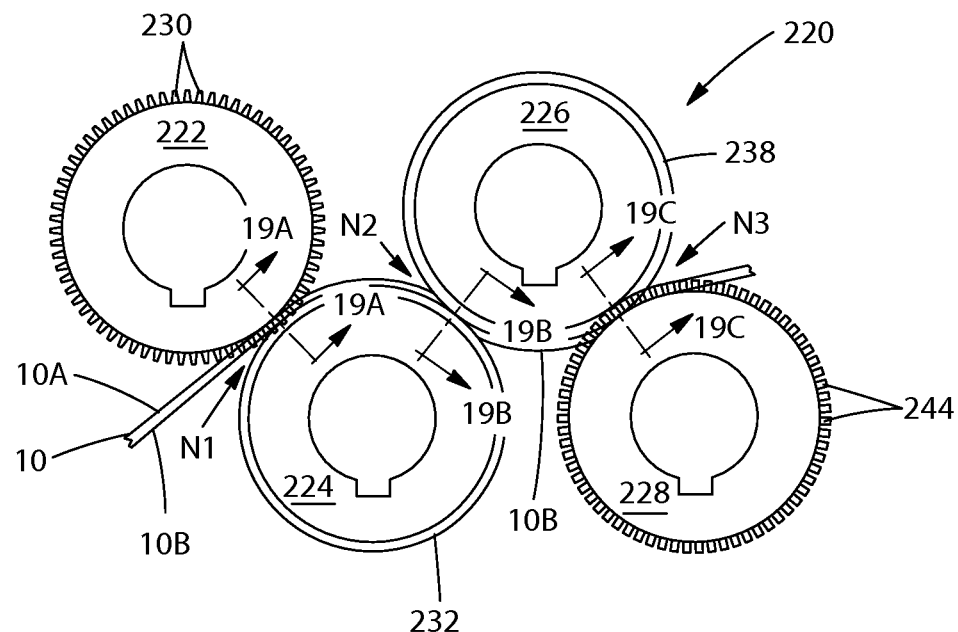
FIG. 19 is a schematic side view of another embodiment of a method and apparatus for deforming a web.

FIG. 19 shows a non-limiting example of an apparatus 220 and process that is used to deform a web so that subsequent deformations are formed in a different orientation and at a different CD location than prior deformations. Such a process may be used to achieve tighter spacing between deformations than might otherwise be possible, particularly in those processes with rolls containing ridges and grooves.

Figure 19A:
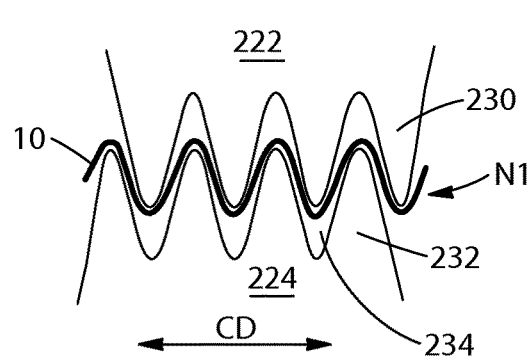
FIG. 19A is an enlarged partially fragmented cross-sectional view of the teeth of the first and second rolls of the apparatus shown in FIG. 19 taken along lines 19A-19A.
Figure 19B:
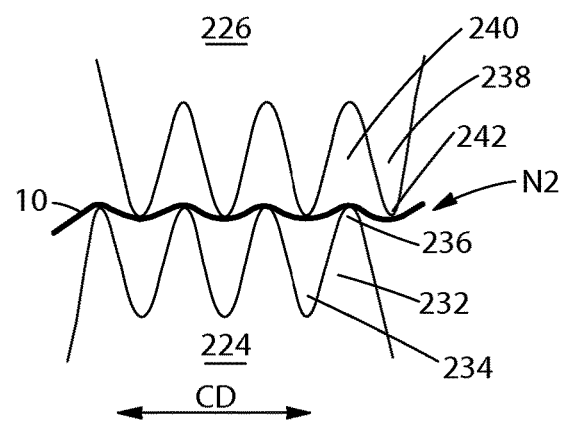
FIG. 19B is an enlarged partially fragmented cross-sectional view of the teeth of the second and third rolls of the apparatus shown in FIG. 19 taken along lines 19B-19B.
Figure 19C:
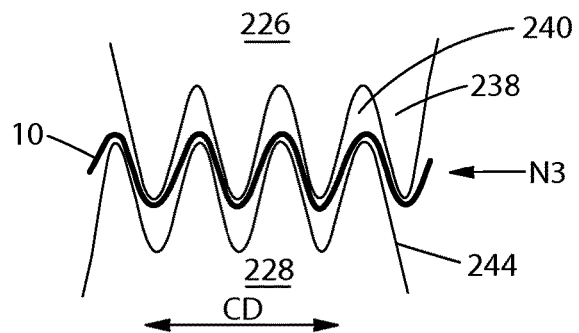
FIG. 19C is an enlarged partially fragmented cross-sectional view of the teeth of the third and fourth rolls of the apparatus shown in FIG. 19 taken along lines 19C-19C.

The apparatus 220 shown in FIG. 19 comprises four rolls, 222, 224, 226, and 228. The apparatus 220 shown in FIG. 19 is similar to the apparatus shown in FIG. 16, except with respect to the alignment of the rolls in the nip N2 between the second and third rolls 224 and 226. The rolls forming the nip N2 are arranged in an offset manner, rather than in a tip-to-tip manner. The second and third rolls 224 and 226 are of configurations that are capable of at least partially intermeshing. In the embodiment shown in FIG. 19, the second and third rolls, 224 and 226, can comprise surfaces with discrete and/or continuous forming elements thereon. The nips between the various rolls of the apparatus 220 shown in FIG. 19 are shown in FIGS. 19A, 19B, and 19C. As shown in FIG. 19A, the first nip N1 between the first and second rolls 222 and 224 may be similar to the first nip of the apparatus shown in FIG. 16. The forming elements 230 on the first roll 222 intermesh with the (projections 232 and) recesses 234 on the second roll 224. FIG. 19B shows the second nip N2 between the second and third rolls 224 and 226. As shown in FIG. 19B, the second and third rolls 224 and 226 are not aligned with the elements thereon in a tip-to-tip alignment as in the case of apparatus shown in FIG. 16, but are instead aligned so that the tips 236 and 242, respectively, of the elements on one of the rolls align with the grooves 240 and 234, respectively, on the opposing roll. The registration of the second and third rolls 224 and 226, however, does not require that the tips 236 and 242, respectively, of the elements on one of the rolls align exactly with the center of the grooves on the opposing roll. The tips of the elements can be offset from the center of the grooves on the opposing roll, if desired. As shown in FIG. 19C, the third nip N3 between the third and fourth rolls 226 and 228 is similar to that in the apparatus shown in FIG. 16. The difference in alignment of the second and third rolls 224 and 226 causes the alignment of the forming elements 244 on the fourth roll 228 to be shifted (such as a distance of up to one-half pitch) relative to the alignment in apparatus shown in FIG. 16. The intermediate second and third rolls 224 and 226 can be aligned to provide any suitable shift in the alignment of the forming elements 244 on the fourth roll 228 (and, thus, the web 10 deformed thereby) up to one-half the pitch between the forming elements on the roll used to form the first set of features.

Figure 20:
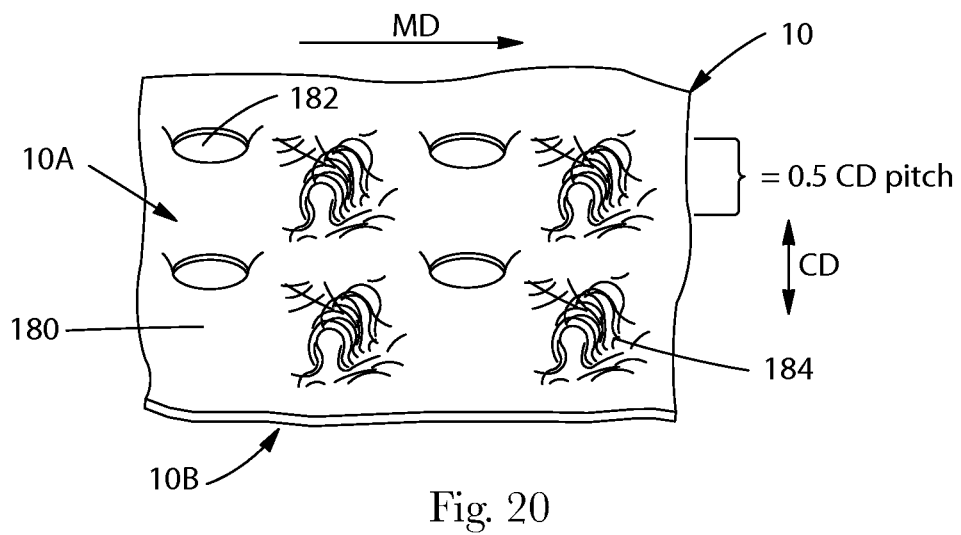
FIG. 20 is a top perspective view of one example of a web that can be formed by using the rolls in FIG. 19.

When the precursor web 10 is fed into the apparatus shown in FIG. 19, in the first nip N1 (shown in FIG. 19A), the precursor web 10 is deformed in a first location to form a first set of formed features in the web, such as the three dimensional apertures 182 shown in FIG. 20. The apertures 182 extend outward from the second surface 10B of the web (downward in FIG. 20). The web 10 is then fed into the second nip N2 (shown in FIG. 19B) in order to contact the web 10 and transfer the precursor web 10 from the second roll 224 to the third roll 226. The third roll 226 has a surface with a plurality of outwardly-extending male elements 238 on its surface. As shown in FIG. 19B, the rolls are arranged so that the outwardly-extending male elements 232 on the second roll 224 are aligned in a cross-machine direction between the outwardly-extending male elements 238 on the third roll 226, and the second surface 10B of the web faces outward on the third roll 226. The third roll 226 either: (i) does not intermesh with the second roll; or (ii) intermeshes with the second roll but not to the extent that the precursor web 10 will be permanently deformed in the second nip N2. The web 10 is then fed into a third nip N3 (shown in FIG. 19C) between the third roll 226 and the fourth roll 228. The fourth roll 228 has forming elements 244 on its surface. When the precursor web 10 is fed into the third nip N3, the precursor web 10 is deformed in a second location. In this step, at least some of the forming elements 244 in the third nip N3 deform the first-time deformed precursor web 10 at least partially in different (or second) locations than the precursor web 10 was deformed in the first nip N1. This forms a second set of formed features in the web, wherein the features comprise portions that extend outward from the first surface 10A of the web to form a second time-deformed precursor web 10.

Figure 21:
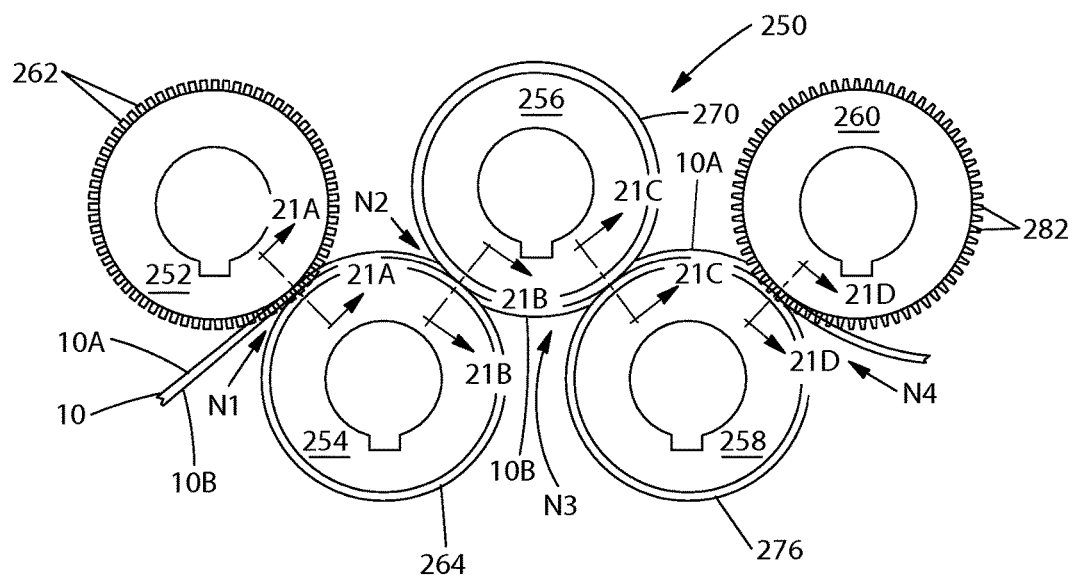
FIG. 21 is a schematic side view of another embodiment of a method and apparatus for deforming a web.
Figure 21A:
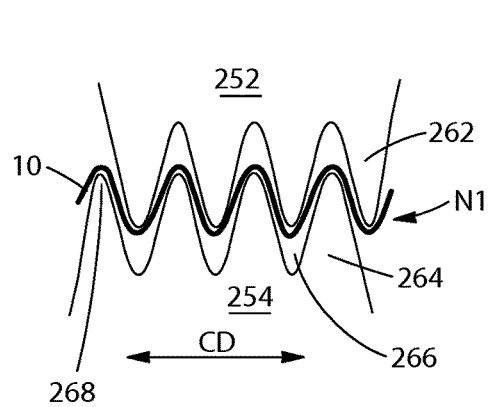
FIG. 21A is an enlarged partially fragmented cross-sectional view of the teeth of the first and second rolls of the apparatus shown in FIG. 21 taken along lines 21A-21A.
Figure 21B:
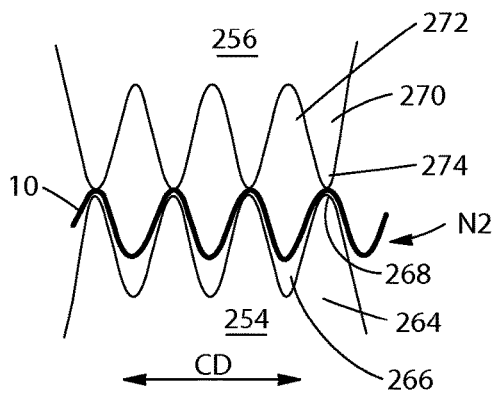
FIG. 21B is an enlarged partially fragmented cross-sectional view of the teeth of the second and third rolls of the apparatus shown in FIG. 21 taken along lines 21B-21B.
Figure 21C:
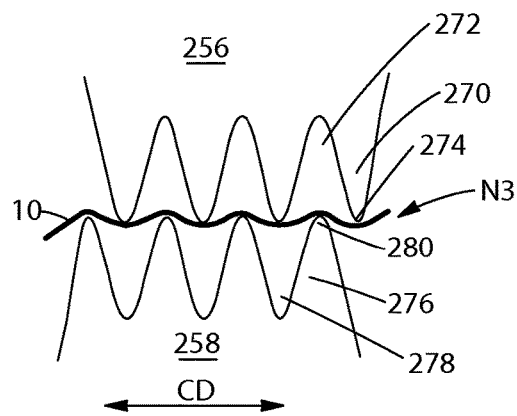
FIG. 21C is an enlarged partially fragmented cross-sectional view of the teeth of the third and fourth rolls of the apparatus shown in FIG. 21 taken along lines 21C-21C.
Figure 21D:
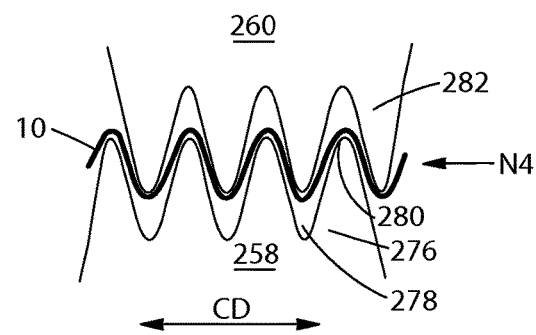
FIG. 21D is an enlarged partially fragmented cross-sectional view of the teeth of the fourth and fifth rolls of the apparatus shown in FIG. 21 taken along lines 21D-21D.

Any suitable combinations of the apparatuses and processes described herein are also possible. FIG. 21, for example shows an embodiment of a process and apparatus that combines some of the features in the processes shown in FIGS. 16 and 19. In this embodiment, the apparatus 250 has five rolls 252, 254, 256, 258, and 260. The process carried out on this apparatus comprises initially feeding the precursor web 10 into a first nip N1 that is formed between a first pair of generally cylindrical intermeshing rolls. The first pair of intermeshing rolls comprises a first roll 252 and a second roll 254. The first roll 252 has a surface with discrete male forming elements 262 thereon, and the second roll 254 has a surface with projections 264 and/or recesses 266 thereon, wherein any projections 264 or the portions of the second roll between any recesses form the radially outwardmost portions 268 on the surface of the second roll 254. When the precursor web 10 is fed into the first nip N1 (shown in FIG. 21A), the precursor web 10 is deformed in a first location to form a first set of formed features in the web. The first set of formed features comprises portions that extend outward from the second surface 10B of the web. The precursor web 10 is then fed into the second nip N2 (shown in FIG. 21B) to contact the web 10 and transfer the web 10 from the second roll 254 to the third roll 256. The third roll 256 has a surface with projections 270 and/or recesses 272 thereon, wherein any projections 272 or the portions of the roll between any recesses form the radially outwardmost portions 274 on its surface. The third roll 256 does not intermesh with the second roll 254. The rolls are arranged so that the outwardmost portions 268 on the second roll 254 substantially align with the outwardmost portions 274 on the third roll 256 to perform a tip-to-tip transfer of the web 10, and the second surface 10B of the web faces outward on the third roll 256. The precursor web 10 is then fed into a third nip N3 (shown in FIG. 21C) to contact the web 10 and transfer the web from the third roll 256 to the fourth roll 258. The fourth roll 258 has a surface with projections 276 and/or recesses 278 thereon, wherein any projections or the portions of the fourth roll 258 between any recesses form the radially outwardmost portions 280 on its surface. The rolls are arranged so that the outwardmost portions 274 on the third roll 256 are aligned in a cross-machine direction between the outwardmost portions 280 on the fourth roll 258, and the first surface 10A of the web faces outward on the fourth roll 258. The web 10 is then fed into a fourth nip N4 (shown in FIG. 21D) between the fourth roll 258 and a fifth roll 260. The fifth roll 260 has forming elements 282 on its surface. When the web 10 is fed into the fourth nip N4, the web 10 is deformed in a second location in which at least some of the forming elements 282 in the fourth nip N4 deform the first-time deformed precursor web at least partially in different locations than the web was deformed in the first nip N1 to form a second set of formed features in the web, wherein the features comprise portions that also extend outward from the second surface 10B of the web to form a second time-deformed precursor web. Such an apparatus 250 can be used for numerous purposes including, but not limited to, deforming the web in different CD lanes for increased density of formed features, or intermixing elements that cannot economically be machined into a single roll.

Figure 22:
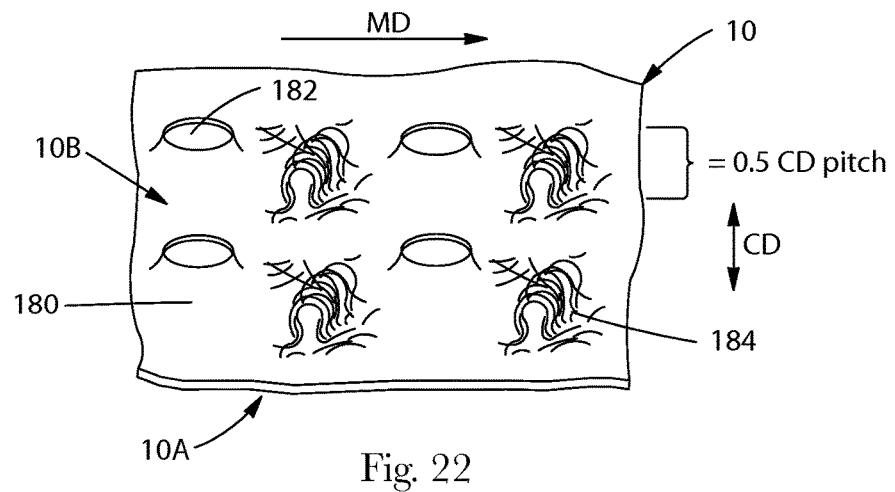
FIG. 22 is a top perspective view of one example of a web that can be formed by using the rolls in FIG. 21.

FIG. 22 shows an embodiment of a nonwoven web 10 made using the apparatus shown in FIG. 21, in which the first roll 252 is a standard CD SELF roll and the fifth roll 260 is a standard RKA roll, and the second, third and fourth rolls are ring rolls. In FIG. 22, the second regions comprise a plurality of spaced apart apertures 182, and the third regions comprise a plurality of spaced apart tufts 184. The apertures 182 and tufts 184 are both pushed out of the plane of the web in the same direction (shown as being upward). As shown in FIG. 22, the apertures 182 are aligned in rows in the MD and the CD. The rows of tufts 184 are, however, aligned between the rows of apertures 182 in the MD and the CD, with the rows of tufts 184 being offset in the CD such that they are separated from the adjacent rows of apertures 182 by a distance of up to one half of the pitch between the apertures 182 in the cross-machine direction (CD).

Figure 23:
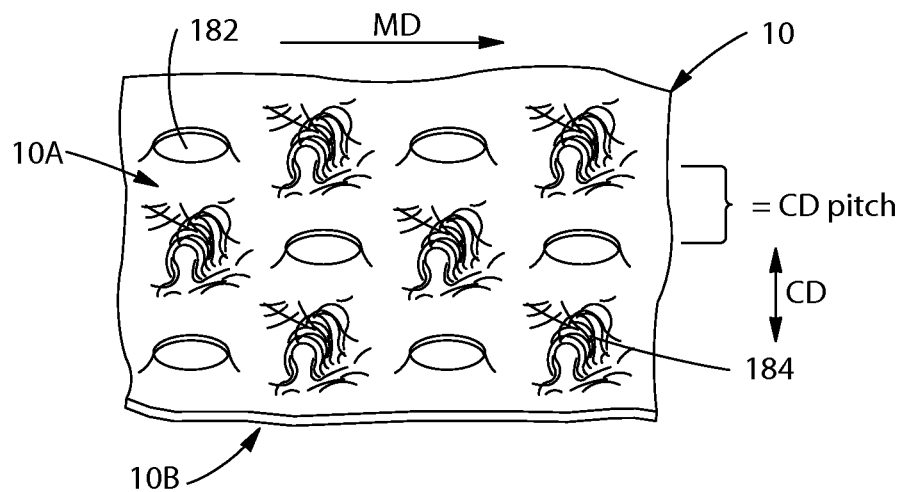
FIG. 23 is top perspective view of one example of a web that can be formed by MD phasing rolls with a staggered pattern using the apparatus shown in FIG. 2 or 4.

FIG. 23 shows an embodiment of a nonwoven web 10 made using a variation of the planetary roll apparatus shown in FIG. 14. In the apparatus used to form the web shown in FIG. 23, the satellite rolls can comprise discrete male forming elements, and the central/sun roll can have continuous (as in grooves) or discrete female elements with which the discrete forming elements can mesh. For example, the central roll can be a ring roll, and the two satellite rolls can comprise a staggered RKA roll and a staggered SELF roll, which are phased in the MD to be offset so they impact the web in different MD locations. In FIG. 23, the second regions comprise a plurality of spaced apart apertures 182, and the third regions comprise a plurality of spaced apart tufts 184. The apertures 182 and tufts 184 are both pushed out of the plane of the web in the same direction (shown as being upward). As shown in FIG. 23, the apertures 182 are aligned in rows in the MD, the CD, and diagonally. The tufts 184 are also aligned in rows in the MD, the CD, and diagonally. However, there are spaces between each of the apertures 182 in the MD and CD rows of apertures 182, and a tuft is located in each of these spaces. In other words, the tufts 184 are intermixed with the apertures 182 and may lie in substantially the same MD and CD rows as the apertures 182 such that the second and third regions alternate in the MD and CD. The tufts 184 are separated from the adjacent rows of apertures 182 by a distance in the cross-machine direction (CD) approximately equal to the pitch between the apertures 182.

C. Alternative Embodiments

Numerous alternative embodiments of the deformed web materials and methods of making the same are possible.

The methods described herein need not always be used to produce intermixed sets of elements that are in different locations on a web. In alternative embodiments, the method can, for example, comprise feeding a web through a "nested roll" arrangement in which at least two of the rolls define two or more nips thereon with other rolls, and the apparatus can be configured to deform the web in the same location at each nip. Such an apparatus and method can be used to lower the strain rate on the areas of the web that are impacted to produce deformations. For example, it may be desirable to initially deform the web to a degree in an initial nip, and then deform the web to a greater degree in a subsequent nip.

In some alternative embodiments, the method can comprise feeding a web through an apparatus with multiple deformation nips, and the apparatus can be configured to deform the web in the same location, but on the opposite surface of the web. This could be useful for reducing the density of drylap or other wetlaid structures.

In other alternative embodiments, the method can comprise feeding a web through an apparatus with multiple deformation nips, and the apparatus can be configured to deform the web in the same location and on the same surface of the web, but the size and/or shape of the forming elements in the first deformation nip is different from that of the forming elements in the subsequent deformation nip. Such an apparatus could, for example, be used to initially form a formed element (such as a three-dimensional region with an aperture, a protrusion, or depression) at a first nip, and then, at a second nip, to make the formed element larger, or of a different shape.

In other embodiments, deformed web materials can be provided which have different regions across their surface with different features therein. For example, a deformed web material can be provided which has a first region with a first combination of features (such as tufts extending upward that are intermixed with downwardly extending tufts), and a second region with a second combination of features (such as upwardly-oriented tufts and downwardly-oriented apertures).

Figure 24:
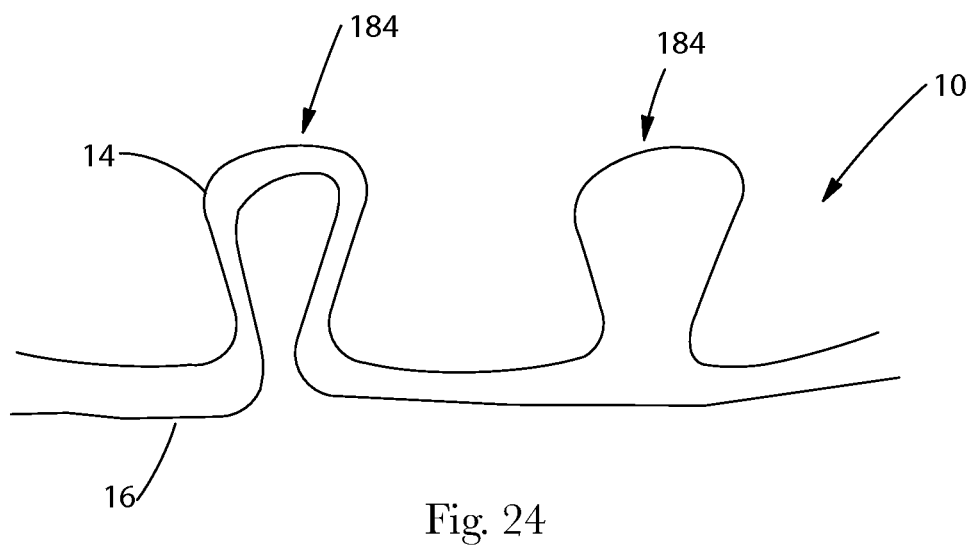
FIG. 24 is a schematic side view of a web that comprises a laminate of a nonwoven and film in which the film is located within one of the tufts and is not formed within another tuft.

In any of the embodiments described herein, the web can comprise one or more layers. Additional webs may be introduced at any of the different nips. The additional layers may be used to add webs having different chemical compositions, formulations, aesthetics, conductive properties, aromatic properties, and mechanical properties. Such additional webs may be selected so that they may or may not span the entire width of the web or webs that were introduced upstream of such additional web(s). This may be used to create a laminate in which some regions of the laminate contain a different number of layers from other regions. In other laminate structures, the regions may contain the same number of layers, but some deformed features could have a different number of layers through their thickness. For example, tufts could be formed into a nonwoven web material 14 in a first nip, and then a film 16 could be introduced in a second nip downstream of the first nip. Such a method could be used to form film/nonwoven tufts in a second nip. As shown in FIG. 24, the overall laminate may comprise some tufts 184 with a nonwoven with a film spanning below the tufts (in those locations not impacted by forming elements in the second nip), while other tufts (impacted by the forming elements in the second nip) will contain both the film and nonwoven within the tuft. Numerous variations of such a method, and the resulting structures are possible, depending on the forming elements and the type and order of introduction of the different webs. The multi-hit process described herein enables independent control of the features formed in a multi-layer structure, providing additional control over the function and aesthetics of the features.

In another alternative embodiment, the method can comprise feeding a web through an apparatus that comprises multiple nips formed by SELF rolls in order to more gradually strain a web than is possible with ring rolling processes. SELF rolls are known to more gradually strain a web than ring rolls, since less material is locked into the tooth and constrained during the deformation step. The apparatus can be configured to deform the web in multiple discrete locations such as in a first location on the web, then immediately adjacent to the first location. The deformation steps are repeated until all the regions within a row are deformed and form a continuous band of deformations that resemble a ring rolled web. The SELF rolls in such an apparatus can comprise CD, MD, or staggered CD or MD SELF rolls. The rolls in such an apparatus will typically all be either CD or MD SELF rolls. The depth of engagement of the SELF teeth in such an embodiment may, but need not, be increased in downstream nips.

Examples

In one non-limiting example for making inter-mixed apertures and tufts oriented in opposite directions in a nonwoven web material, like that shown in FIG. 15, an apparatus can be used that comprises a 80 pitch raised ridge RKA roll intermeshed with a 80 pitch SELF roll, like that shown in FIG. 14C. When a number, such as "80" is given to describe the pitch, this refers to the number in thousands of an inch (0.0254 mm). The nonwoven material can have any suitable basis weight, down to about 15 gsm. In this example, it comprises a 28 gsm spunbonded polyethylene sheath/polypropylene core bicomponent fiber nonwoven. The raised ridge RKA roll has discrete forming elements that are oriented so the long direction runs in the MD. The teeth are arranged in a standard pattern, meaning adjacent teeth align in rows in the CD. The teeth on the RKA roll have a pyramidal shape with 6 sides that taper from the base to a sharp point at the tip. The tooth height TH is 0.270 inch (6.9 mm), the ridge height is 0.170 inch (4.3 mm), the side wall angle on the long side of the tooth is about 5 degrees and the side wall angle of the leading and trailing edges of the teeth is 28.5 degrees. The RKA roll comprises teeth that are evenly spaced in the MD, with a tip to tip spacing in the MD of 0.320 inch (8.1 mm) and a CD pitch P of 0.080 inch (2 mm). The teeth on the SELF roll are also arranged in a standard pattern and are oriented such that the long direction runs in the MD. The teeth have a uniform circumferential length dimension TL of about 0.080 inch (2 mm) measured generally from the leading edge LE to the trailing edge TE, a tooth tip radius TR at the tooth tip of about 0.005 inch (0.13 mm), are uniformly spaced from one another circumferentially by a distance TD of 0.240 inch (6.1 mm), and have a tooth height TH of about 0.270 inch (6.9 mm). The long sides of the teeth have a side wall angle of about 3 degrees, and the leading and trailing edges of the teeth have vertical side walls. Both rolls have a diameter of about 5.7 inch (14.5 cm) and are heated to a temperature of 130 deg C. The RKA and the SELF roll are aligned in the CD such that the clearances on either side of the teeth are about equal. The RKA and SELF rolls are MD phased such that the forming teeth on the SELF roll align with the raised ridges on the RKA roll, and the rolls are engaged to a depth of 0.250 inch (6.4 mm).

Figure 16B:
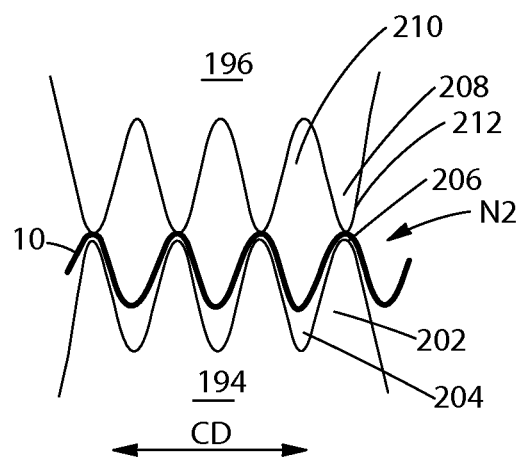
FIG. 16B is an enlarged partially fragmented cross-sectional view of the teeth of the second and third rolls of the apparatus shown in FIG. 16 taken along lines 16B-16B.
Figure 16C:
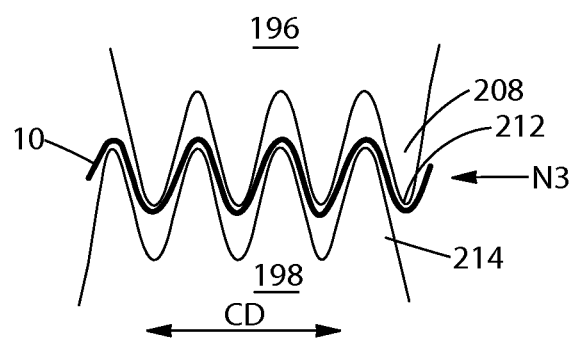
FIG. 16C is an enlarged partially fragmented cross-sectional view of the teeth of the third and fourth rolls of the apparatus shown in FIG. 16 taken along lines 16C-16C.

In a second non-limiting example for making inter-mixed apertures and tufts oriented in opposite directions in a nonwoven web material, like that shown in FIG. 17, a 4-roll nested apparatus with a tip-tip transfer roll can be used, such as that shown in FIG. 16. The nonwoven material can have any suitable basis weight, down to about 15 gsm. In this example, it comprises a 28 gsm spunbonded polyethylene sheath/polypropylene core bicomponent fiber nonwoven. The first nip N1 comprises a 100 pitch staggered RKA roll intermeshed with a 100 pitch ring roll at 0.200 inch (5.1 mm) depth of engagement. The teeth on the RKA roll have a pyramidal shape with six sides that taper from the base to a sharp point at the tip and are oriented so the long direction runs in the MD. The teeth are arranged in a staggered pattern, with a CD pitch P of 0.100 inch (2.5 mm) and a uniform tip to tip spacing in the MD of 0.250 inch (6.5 mm). The tooth height TH is 0.270 inch (6.9 mm), the side wall angle on the long side of the tooth is 4.7 degrees and the side wall angle of the leading and trailing edges of the teeth is 22.5 degrees. The 100 pitch ring roll also has a CD pitch P of 0.100 inch, a tooth height TH of 0.270 inch, a tip radius TR of 0.005 inch, and a side wall angle of 4.7 degrees. The RKA roll and ring roll are aligned in the CD such that the clearances on either side of the teeth are about equal. The second nip N2 comprises a 100 pitch ring roll aligned with a second 100 pitch ring roll, in a tip-tip configuration (as shown in FIG. 16B) with a −0.050″ (−1.25 mm) depth of engagement. The third nip N3 comprises a 100 pitch ring roll intermeshed with a 100 pitch SELF roll at 0.135 inch (3.4 mm) depth of engagement. The teeth on the 100 pitch SELF roll form a staggered pattern, are oriented such that the long dimension runs in the MD, and have a CD pitch P of about 0.100 inch. The teeth have a uniform circumferential length dimension TL of about 0.120 inch (3 mm) measured generally from the leading edge LE to the trailing edge TE, a tooth tip radius TR at the tooth tip of about 0.005 inch (0.127 mm), are uniformly spaced from one another circumferentially by a distance TD of about 0.130 inch (3.3 mm), and have a tooth height TH of about 0.270 inch (6.9 mm). The long sides of the teeth have a side wall angle of about 4.7 degrees, and the leading and trailing edges of the teeth have vertical side walls. The SELF roll and ring roll are aligned in the CD such that the clearances on either side of the teeth are about equal. All four rolls (RKA roll, SELF roll, two ring rolls) have a diameter of about 5.7 inches (14.5 cm). The SELF and RKA rolls are MD phased such that the tufts are formed approximately half-way between the apertures in the MD.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "90°" is intended to mean "about 90°".

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web comprising:
   a first side and a second side;
   land areas having a web density;
   formed discrete first protrusions disposed in a plurality of spaced apart first locations, wherein the formed discrete first protrusions have a density that is permanently altered to be different than the web density in response to an applied stress or strain; and
   formed discrete second protrusions disposed in a plurality of spaced apart second locations that are different locations than the first locations, such that the second protrusions are distributed between the first protrusions, with respect to an X-Y dimension in a plane of the web, wherein the formed discrete second protrusions have a density that is permanently altered to be different than the web density in response to an applied stress or strain;
   apertures defined at distal ends of the formed discrete second protrusions; and
   wherein the first protrusions extend out from a first side of the web and the second protrusions extend out from a second side of the web.

2. The nonwoven web of claim 1 wherein the first protrusions and the second protrusions have different shapes when taken from a plan view.

3. The nonwoven web of claim 1 wherein the first protrusions and the second protrusions have different sizes.

4. The nonwoven web of claim 1 wherein the first protrusions and the second protrusions have different aspect ratios.

5. The nonwoven web of claim 1 wherein the first protrusions and the second protrusions have different spacings.

6. The nonwoven web of claim 1 wherein the first protrusions and the second protrusions have different heights.

7. The nonwoven web of claim 1 wherein the first protrusions and the second protrusions have different densities.

8. The nonwoven web of claim 1 wherein the first protrusions and the second protrusions have different surface treatments.

9. The nonwoven web of claim 1 wherein the first protrusions and the second protrusions include different numbers of layers from the web.

10. The nonwoven web of claim 1 wherein the first protrusions are tufts and the second protrusions have a columnar shape.

11. The nonwoven web of claim 10 wherein the tufts are open on at least one end.

12. The nonwoven web of claim 1 wherein the first protrusions are tufts and the second protrusions have a shape selected from the group including: dome-shaped, tent-shaped, and volcano-shaped.

13. The nonwoven web of claim 12 wherein the tufts are open on at least one end.

14. The nonwoven web of claim 1 wherein the first protrusions have a columnar shape and the second protrusions have a shape selected from the group including: dome-shaped, tent-shaped, and volcano-shaped.

15. The nonwoven web of claim 1 wherein a center-to-center spacing between the first and the second protrusions is less than or equal to 10 millimeters.

16. The nonwoven web of claim 1 wherein a center-to-center spacing between the first and the second protrusions is less than or equal to 5 millimeters.

17. The nonwoven web of claim 1 wherein, for at least a portion of the web, the total number of protrusions is 4-100 protrusions per square inch.

18. The nonwoven web of claim 1 wherein, for at least a portion of the web, the total number of protrusions is 4-25 protrusions per square inch.

19. A nonwoven web comprising:
    a first side and a second side;
    land areas having a web density;
    formed discrete first protrusions disposed in a plurality of spaced apart first locations, wherein the formed discrete first protrusions have a density that is permanently altered to be different than the web density in response to an applied stress or strain;
    formed discrete second protrusions disposed in a plurality of spaced apart second locations that are different locations than the first locations, such that the second protrusions are distributed between the first protrusions, with respect to an X-Y dimension in a plane of the web, wherein the formed discrete second protrusions have a density that is permanently altered to be different than the web density in response to an applied stress or strain;
    apertures defined at distal ends of the formed discrete second protrusions;
    wherein the first protrusions extend out from a first side of the web and the second protrusions extend out from a second side of the web; and
    wherein the first protrusions and the second protrusions have different densities.

* * * * *